United States Patent [19]
Ares, Jr. et al.

[11] Patent Number: 5,773,244
[45] Date of Patent: Jun. 30, 1998

[54] METHODS OF MAKING CIRCULAR RNA

[75] Inventors: Manuel Ares, Jr., Santa Cruz, Calif.; Ethan E. Ford, Harbor, N.Y.

[73] Assignee: Regents of the University of California, Oakland, Calif.

[21] Appl. No.: 431,896

[22] Filed: May 1, 1995

Related U.S. Application Data

[63] Continuation-in-part of Ser. No. 63,857, May 19, 1993, abandoned.

[51] Int. Cl.[6] .............................. C12P 21/00; C12P 19/34; C12N 15/00; C07H 21/02
[52] U.S. Cl. .................... 435/69.1; 435/91.1; 435/91.21; 435/91.3; 435/91.31; 435/91.4; 435/91.42; 435/172.1; 435/172.3; 435/252.3; 435/254.2; 435/254.21; 435/320.1; 536/23.1
[58] Field of Search .............................. 435/69.1, 71.1, 435/91.1, 91.3, 91.31, 91.4, 91.42, 172.1, 172.3, 199, 320.1, 91.21, 91.5, 240.1, 240.2, 240.4, 252.3, 254.2, 254.21; 514/44; 530/300, 350; 536/23.1

[56] References Cited

U.S. PATENT DOCUMENTS

| 4,987,071 | 1/1991 | Cech et al. | 435/91.31 |
| 5,093,246 | 3/1992 | Cech et al. | 435/6 |
| 5,354,855 | 10/1994 | Cech et al. | 536/24.1 |

OTHER PUBLICATIONS

Chan et al. "Stability of group I intron RNA in *Escherichia coli* and its potential application in a novel expression vector" Gene 73:295–304, 1988.
Salvo et al. J. Mol. Biol. 211: 537–549, 1990.
Horsch et al. "A simple and general method for transferring genes into plants" Science 227: 1229–1231, Mar. 1985.
Rossi et al. "RNA enzymes (ribozymes) as antiviral therapeutic agents" Trends in Biotechnology 8: 179–183, Jul. 1990.
Russo et al. "Transcription terminates near poly(A) site in the CYC1 gene of the yeast *Saccharomyces cerevisiae*" Proc. Natl. Acad. Sci. USA 86: 8348–8352, Nov. 1989.
Ethan Ford, et al., "Synthesis of circular RNA in bacteria and yeast using RNA cyclase ribozymes derived from a group I intron of phage T4", *Proc. Natl. Acad. Sci.*, USA, vol. 91, pp. 3117–3121, Apr. 1994.
Chang–you Chen, et al., "Initiation of Protein Synthesis by the Eukaryotic Translational Apparatus on Circular RNAs", *Science*, vol. 268, Apr. 28, 1995, pp. 415–417.

(List continued on next page.)

*Primary Examiner*—John L. LeGuyader
*Assistant Examiner*—Thomas G Larson
*Attorney, Agent, or Firm*—Townsend and Townsend and Crew LLP

[57] ABSTRACT

A prototype RNA cyclase ribozyme that allows efficient production of circular RNA. Methods for modifying the prototype to produce a wide variety of custom circular RNA are detailed. The method utilizes a new plasmid which enables production of a wide variety of imaginable RNA sequences in a covalent, circular form free from intron sequences in vitro. At a particular site in the plasmid, a sequence coding for the desired circular RNA is inserted to create a new RNA cyclase ribozyme gene. RNA transcribed from RNA cyclase ribozyme genes autocatalytically converts the desired RNA sequence it contains into circular form. RNA cyclase genes may be placed into appropriate expression vectors for synthesis of circular RNA in vivo as part of ribozyme or antisense gene regulation approaches to genetic engineering.

26 Claims, 14 Drawing Sheets

OTHER PUBLICATIONS

*RNA Processing Program and Abstracts,* RNA Processing Meeting, Keystone, Colorado, May 25–31, (1992).

M. Putiaraju and Michael D. Been, "Group I permuted intron–exon (PIE) sequences self–splice to produce circular exons", *Nucleic Acids Research*, vol. 20, No. 20, 5357–5364.

Kevin A. Jarrell, "Inverse splicing of a group II intron", *Proc. Nat'l Acad. Sci. USA,* vol. 90, pp. 8624–8627, Sep. 1993.

Price, J.V. et al., "5'Exon Requirement for Self–splicing of the *Tetrahymena thermophila* Pre–ribosomal RNA and Identification of a Cryptic 5' Splice Site in the' Exon." *J. Mol. Biol.,* 196, 49–60 (1987):.

Cech, T.R., "Self–Splicing of Group I Introns" *Annu. Rev. Biochem.* 59:543–68 (1990).

Galloway Salvo, J.L., et al., "Deletion–tolerance and *Trans*–splicing of the Bacteriophage T4 td Intron Analysis of the P6–L6a Region" *J. Mol. Biol.,* 211, 537–549 (1990).

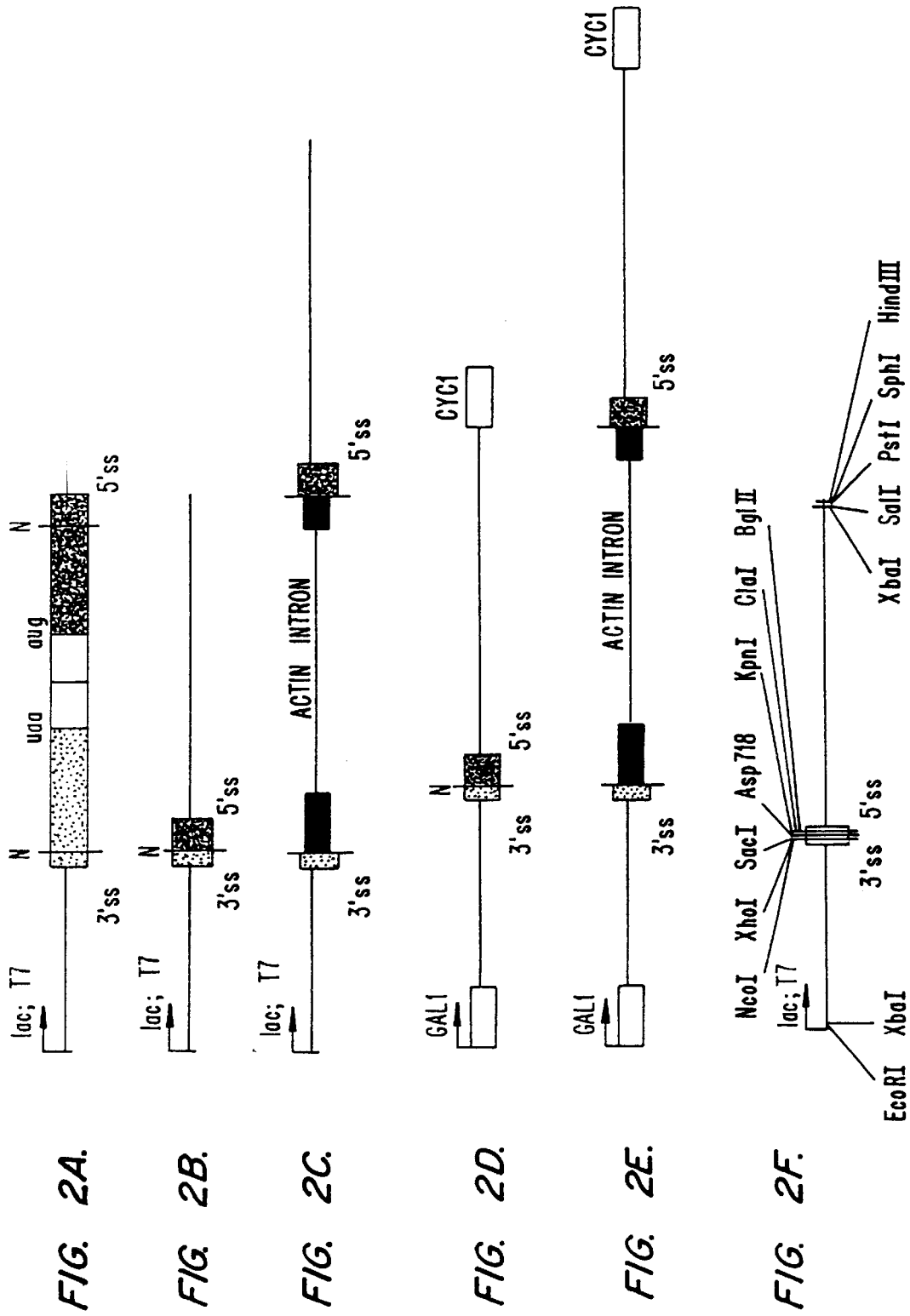

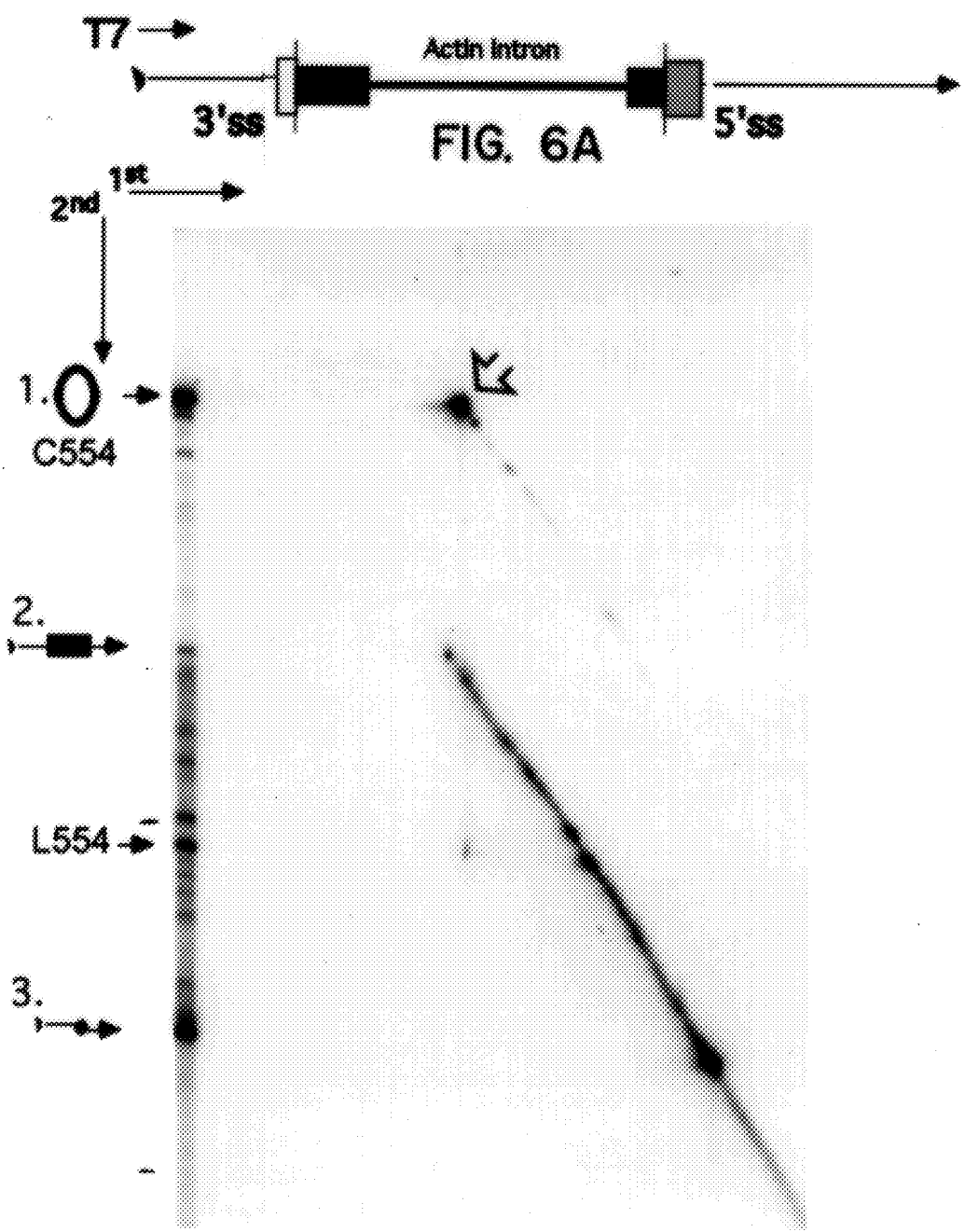

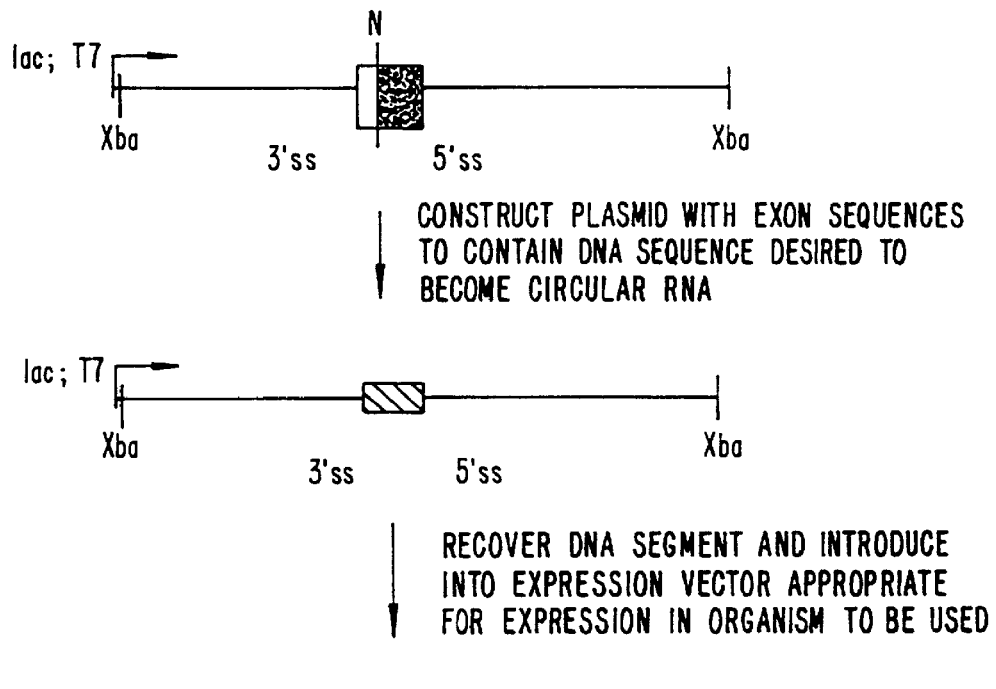
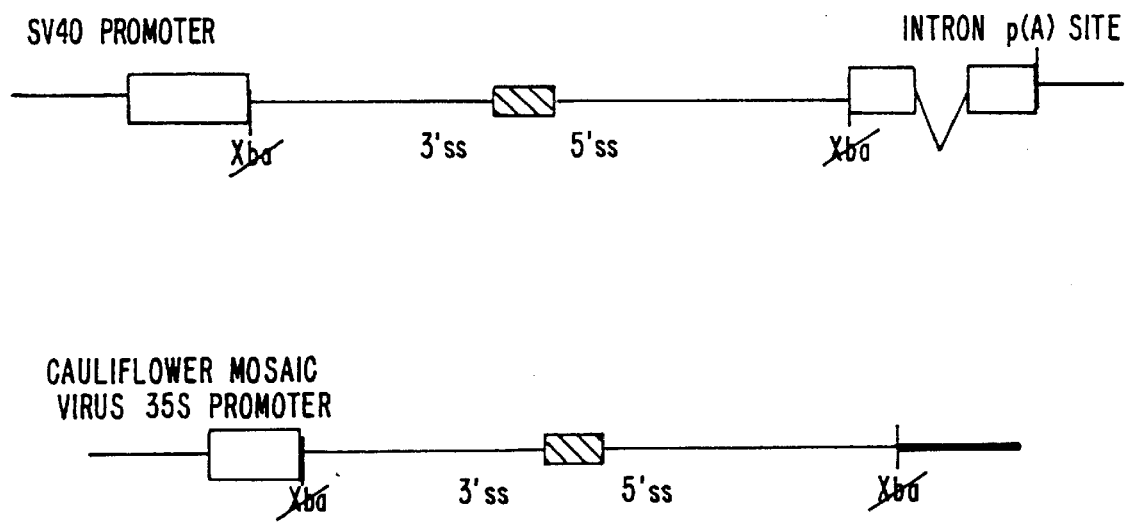
FIG. 11.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 510 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:1:

```
GGGAAUUCUA  GAGAAAAUUU  CGUCUGGAUU  AGUUACUUAU  CGUGUAAAAU  CUGAUAAAUG      60
GAAUUGGUUC  UACAUAAAUG  CCUAACGACU  AUCCCUUUGG  GGAGUAGGGU  CAAGUGACUC     120
GAAACGAUAG  ACAACUUGCU  UUAACAAGUU  GGAGAUAUAG  UCUGCUCUGC  AUGGUGACAU     180
GCAGCUGGAU  AUAAUUCCGG  GGUAAGAUUA  ACGACCUUAU  CUGAACAUAA  UGCUACCGUU     240
UAAUAUUGCG  UCAUAUGUUC  UAUCAGUUUA  AUGUGCGUAA  UGGCUAUUUG  GAUUUGCAGU     300
GGUAUCAACG  CUCAGUAGAU  GUUUUCUUGG  GUUAAUUGAG  GCCUGAGUAU  AAGGUGACUU     360
AUACUUGUAA  UCUAUCUAAA  CGGGGAACCU  CUCUAGUAGA  CAAUCCCGUG  CUAAAUUGUA     420
GGACUGCCCU  UUAAUAAAUA  CUUCUAUAUU  UAAAGAGGUA  UUUAUGAAAA  GCGGAAUUUA     480
UCAGAUUAAA  AAUACUUUCU  CUAGAGUCGA                                        510
```

( 2 ) INFORMATION FOR SEQ ID NO:2:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: circular ( i i ) MOLECULE TYPE: RNA ( x i ) SEQUENCE DESCRIPTION: SEQ ID NO:2:

```
CUACCGUUUA  AUAUUGCGUC  AUAUGUUCUA  UCAGUUUAAU  GUGCGUAAUG  GCUAUUUGGA      60
UUUGCAGUGG  U                                                              71
```

(2) INFORMATION FOR SEQ ID NO:3:

(i) SEQUENCE CHARACTERISTICS:
  (A) LENGTH: 100 base pairs
  (B) TYPE: nucleic acid
  (C) STRANDEDNESS: single
  (D) TOPOLOGY: circular (ii) MOLECULE TYPE: RNA (xi) SEQUENCE DESCRIPTION: SEQ ID NO:3:

```
CUACCGUUUA AUAUUGCGUC AUAUGUUCUA UCAGUUUAAU GUGCGUAAUG GCUAUUUGGA      60
UUUGCAGUGG UAUCAACGCU CAGUAGAUGU UUUCUUGGGU                           100
```

(2) INFORMATION FOR SEQ ID NO:4:

(i) SEQUENCE CHARACTERISTICS:
  (A) LENGTH: 66 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:4:

```
CATAATGCTA CCATGGAGCT CGAGGTACCA TCGATAGATC TCAGGTCAAT TGAGGCCTGA      60
GTATAA                                                                66
```

(2) INFORMATION FOR SEQ ID NO:5:

(i) SEQUENCE CHARACTERISTICS:
  (A) LENGTH: 39 base pairs
  (B) TYPE: nucleic acid
  (C) STRANDEDNESS: single
  (D) TOPOLOGY: circular (ii) MOLECULE TYPE: RNA (xi) SEQUENCE DESCRIPTION: SEQ ID NO:5:

```
CUACCAUGGA GCUCGAGGUA CCAUCGAUAG AUCUCAGGU                             39
```

(2) INFORMATION FOR SEQ ID NO:6:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:6:

```
AAATCCAAAT AGCCATTAC                                                   19
```

(2) INFORMATION FOR SEQ ID NO:7:

(i) SEQUENCE CHARACTERISTICS:
  (A) LENGTH: 64 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:7:

```
CTCAGGCCTC AATTGACCTG AGATCTATCG ATGGTACCTC GAGCTCCATG GTAGCATTAT      60
GTTC                                                                  64
```

METHODS OF MAKING CIRCULAR RNA

This application is a continuation-in-part of U.S. Ser. No. 08/063,857, filed May 19, 1993 (now abandoned), which is incorporated herein by reference in its entirety for all purposes.

The present invention was made in the course of research supported by the research grants RO1 GM 40478 and KO4 GM 00546 from the National Institute of General Medical Sciences, National Institutes of Health. The United States Government may have certain rights in this invention.

BACKGROUND OF THE INVENTION

1. Field of Invention

This invention concerns a method for construction of ribozymes that produce RNA in a circular form. The method utilizes a new plasmid which enables custom production of RNA sequences in a covalent, circular form. A DNA sequence for the desired circular RNA is inserted into the plasmid to create a gene encoding the RNA cyclase ribozyme required to produce the desired circular RNA. The created RNA cyclase ribozyme gene may be excised and inserted into desired expression vectors for production of circular RNA in eukaryotic and prokaryotic cells. In particular, the invention concerns the method comprising a rearrangement and conversion of the self-splicing group I intron from the bacteriophage T4 td gene into a prototype RNA cyclase ribozyme gene. The prototype RNA cyclase is easily modified to produce custom circular RNAs of many different sequences. The invention further concerns efficient production of circular RNA in vitro and in vivo. Circular RNA of this invention is useful in the design of stable forms of RNA used as regulators of gene expression, and for structure and function studies of RNA.

2. Background Art and Related Disclosures

Circular RNA is useful in the design and production of stable form of RNA used as regulators of gene expression and as a messenger RNA to direct synthesis of long, multiply repeating protein chains. Until now, however, it was difficult to produce large quantities of circular RNA which would be free from highly structured and catalytically active intron ribozyme sequences in vitro, and it was impossible to do so at all in vivo.

Prior to this invention there were three main techniques for making circular RNA in vitro. One technique, described for example in *PNAS*, 69:3009 (1972) uses the protein enzyme T4 RNA ligase. The second technique, described in *Science*, 256:992 (1992) relies on the ability of T4 DNA ligase to act as an RNA ligase when the RNA ends to be ligated are held together by an oligonucleotide. Both these techniques suffer from inefficiency and expense due to the large amount of enzyme required. The third technique, described in *Development*, 102:837 (1988) uses the cyclization or circularization activity of group I introns where most of the intron sequences that carry out the reaction must remain a part of the circle. The presence of such a large highly structured nucleic acid sequence severely limits the types of RNA sequences that can be made circular by that technique. In addition, the catalytic activity of the intron may remain and interfere with structure and function of the circular RNA.

The above problems are eliminated by the method of the current invention. The invention relies on a special rearrangement of group I intron elements that perform a splicing reaction rather than an intron cyclization reaction or a protein enzyme reaction. Particularly, the current invention relies on an arrangement of plasmid DNA elements, described below, coding for parts of the group I intron which, after transcription into RNA, is appropriate to make the splicing reaction produce circles. This invention also relies on the ability of this arrangement to function in vivo.

In order to be able to produce a wide variety of different RNAs in circular form in vitro and in vivo, new plasmid vectors needed to be constructed. Plasmids are extrachromosomal genetic elements consisting of a circular duplex of DNA which can replicate independently of chromosomal DNA. Plasmids are used in genetic engineering for gene isolation or as vectors for gene expression. Typically, plasmid vectors are as small as possible with little or no extraneous genetic information. They are self-replicating and well characterized with respect to gene location, restriction enzyme cleavage sites, and nucleotide sequence. The vectors possess a certain number of unique restriction endonuclease cleavage sites. This feature provides maximum flexibility in terms of introducing different kinds of new DNA fragments to a plasmid. A huge number of plasmids exist and new plasmids are constantly being fashioned by additions and deletions to fit particular needs and purposes.

Early evidence that the current invention might be feasible came from studies of group I introns. Group I introns share a complex set of secondary and tertiary structures containing a series of conserved RNA stem loops which form the catalytic core. Many of these introns are self-splicing in vitro, that is they will splice and form two ligated exons as RNA with no accessory protein factors. The products created by the group I autocatalytic reaction are (1) an upstream exon ligated at the 5' splice site to the 3' splice site of a downstream exon and (2) a linear intron that can undergo further reversible auto-catalysis to form a circular intron. This intron circularization reaction is the basis of a previous method and is not to be confused with circularization of the exon sequence that is produced by the current invention. The intron can be broken without substantial loss of function as shown in *J. Mol. Biol.*, 211:537 (1990), which demonstrated that the group I intron could be split into two transcripts which could associate with each other to produce an active intron and carry out splicing. An upstream 3' splice site can be joined to a downstream 5' splice site as indicated by *J. Mol. Biol.*, 196:49 (1987), which showed that a cryptic 5' splice site in the downstream exon was used in a mutant derivative of the Tetrahymena group I intron to produce circles inefficiently.

It is therefore a primary object of the current invention to provide a general method for preparation of a desired RNA in circular form. More specifically, plasmids having a special arrangement of intron elements suitable to perform the splicing are used in a method to prepare such circular RNA.

SUMMARY

One aspect of the current invention is a method for rearrangement of regions that code for RNA splicing elements in such a way that if the 3' half of an intron is placed first, followed by the 3' splice site, followed by the sequence of interest inserted between the 3' splice site and the 5' splice site, followed by the 5' splice site and the 5' half of an intron, then after splicing, the sequence between the 3' splice site and the 5' splice site becomes circular.

Another aspect of the current invention is a plasmid having rearranged regions that code for splicing elements in such a way that the 3' half of an intron is placed first, followed by the 3' splice site, then the sequence desired to be made circular RNA, the 5' splice site and the 5' half of an intron.

Another aspect of the current invention is a rearrangement of plasmid elements appropriate to make the splicing reaction produce circles and the ability of this arrangement to function in vitro and in vivo.

Another aspect of the current invention are new plasmids having rearranged regions that code for splicing elements into which a coding sequence of a wide variety of desired RNAs can be inserted and wherein, when the plasmid is linearized and transcribed, the resulting RNA spontaneously splices out the inserted RNA sequence and circularizes it in vitro.

Another aspect of the current invention is a plasmid having rearranged regions that code for splicing elements into which a coding sequence of a wide variety of desired RNAs can be inserted and wherein, upon expression of the newly rearranged sequences, the resulting RNA spontaneously splices out the inserted RNA sequence and circularizes it in vivo.

Still another aspect of this invention is a method for producing a circular RNA by RNA cyclase ribozyme, said method comprising steps:

(a) identifying a nucleic acid sequence to be made circular;

(b) creating a plasmid having DNA constructs wherein the arrangement of regions that code for ribozyme splicing elements is the 3' half portion of an intron, the 3' splice site, the nucleic acid sequence of step (a), the 5' splice site and the 5' half of the intron wherein the nucleic acid is inserted into an exon sequence of a plasmid using one or two polylinker sites of the exon;

(c) removing undesired exon sequences derived from the polylinker;

(d) expressing the plasmid DNA sequence comprising the rearranged ribozyme elements and the sequence to be made circular as RNA sequence; and (e) allowing the RNA transcripts to selfsplice. Still another aspect of the current invention is a method for making a wide variety of desired RNAs in a covalent, circular form, free from highly structured and catalytically active intron ribozyme sequences, which method is useful in the design of stable forms of RNA regulators of gene expression in vitro, comprising steps:

(a) preparing a plasmid having rearranged regions that code for ribozyme splicing elements in such a way that the 3' half of an intron is placed first, followed by the 3' splice site, followed by sequence desired to be made circular RNA, followed by the 5' splice site and the 5' half of an intron;

(b) modifying the DNA sequences between 3' and 5' splice site to create the sequence to be made circular as RNA by cloning and by oligonucleotide directed mutagenesis techniques;

(c) expressing the DNA sequence comprising the rearranged ribozyme elements and the sequence to be made circular as RNA sequence by using the RNA synthesis in vitro using RNA polymerase; and (d) allowing the RNA sequence including the ribozyme elements to carry out splicing reaction in such a way that the 5' and 3' splice sites are joined to produce a circular RNA in vitro.

Still another aspect of the current invention is a method for making a wide variety of desired RNAs in a covalent, circular form, free from highly structured and catalytically active intron ribozyme sequences, which method is useful in the design of stable forms of RNA regulators of gene expression in vivo, comprising steps:

(a) preparing a plasmid having rearranged regions that code for ribozyme splicing elements in such a way that the 3' half of an intron is placed first, followed by the 3' splice site, followed by the sequence desired to be made circular RNA, followed by the 5' splice site and the 5' half of an intron;

(b) modifying the DNA sequences between 3' and 5' splice site to create the sequence to be made circular as RNA by cloning and oligonucleotide directed mutagenesis techniques;

(c) expressing the DNA sequence, comprising the rearranged ribozyme elements and the sequence to be made circular, as RNA sequence by cloning the DNA sequence into an appropriate expression vector that functions in the organism(s) where the RNA is to be made; and (d) allowing the RNA sequence including the ribozyme elements to carry out splicing reaction in such a way that the 5' and 3' splice sites are joined to produce a circular RNA.

Still yet another aspect of the current invention is a circular RNA produced by the current method in vitro and in vivo.

BRIEF DESCRIPTION OF DRAWINGS

FIG. 2, panels A-F depict the plasmid constructs of the inventions: (A) pEFC, (B) PEFCΔNde, (C) pΔNAct(+), (D) pΔN-Y(+), (E) pΔN-A(+)-G(+), (F) pRR1.

FIG. 6 panels A and B provide, respectively, the structure of and 2D gel analysis for pANact(+) in vitro transcription/splicing reactions.

FIG. 11 is a diagram of the method for creating circular RNA in mammalian and plant cells.

DETAILED DESCRIPTION OF THE INVENTION

Figure 1A:
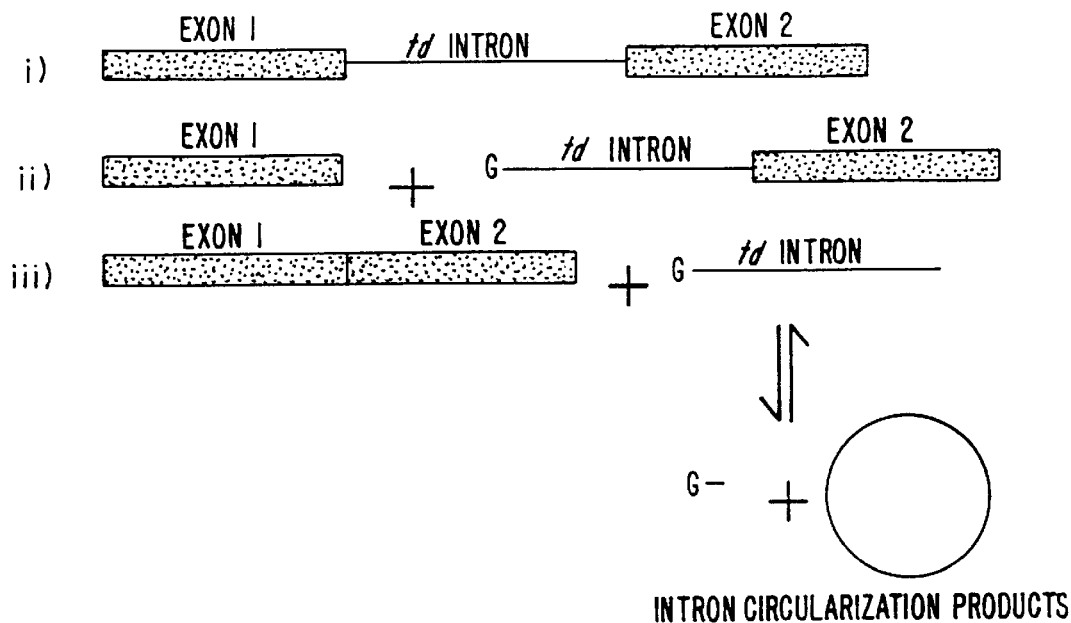
FIG. 1, panels A and B compare normal group I splicing (A) and the RNA cyclase ribozyme of the current invention (B).

The current invention concerns a method for production of wide variety of different desired RNAs in a covalently closed circular form, which RNAs are free from the highly structured RNA elements used to create the circular RNAs using RNA cyclase ribozymes. The invention also concerns a new plasmid containing the special arrangement of intron elements required to produce circular RNA, which plasmid acts as a prototype plasmid that can be modified to create new plasmids encoding new RNA cyclase ribozymes that produce a desired circular RNA. The method is useful in the design of stable forms of RNA used as regulators of gene expression, such as for example, ribozyme or antisense regulators, especially in genetically engineered organisms.

I. Method for Production of Circular RNA Constructs

A. Plasmid

The general purpose of this particular invention was to develop a method for preparation of a wide variety of circular RNA molecules. Consequently, the new plasmid was designed as a prototype which could easily be modified to produce an RNA containing many imaginable RNA sequences in covalent, circular form with as little residual intron sequence as desired. The design relies on the splitting and rearrangement of the splicing elements of an intron to create a prototype RNA cyclase ribozyme gene. A coding sequence for the desired RNA is inserted as a DNA fragment into the plasmid at a special cloning site to create a new plasmid containing a new RNA cyclase gene. After the new plasmid is transcribed into RNA in vitro or in vivo, the new RNA cyclase ribozyme renders the desired RNA circular, using the modified splicing reactions carried out by the intron elements cyclase reaction. This new RNA cyclase gene may be removed from the plasmid and inserted into various expression vectors, depending on where and when the expression of the desired circular RNA is required.

B. Method for Production of Circular RNA

The method generally concerns the creation of plasmids with a split and rearranged intron sequence, so that a continuous exon sequence is flanked by splice sites and partial introns. The exon sequence can be modified to contain an RNA sequence of choice. The created plasmids are transcribed and circular exon RNA is created by the splicing reactions. Production of circular RNA by the method of the current invention has been achieved both in vitro and in vivo.

The method for making circular RNA utilizes a prototype plasmid into which a coding sequence for the desired circular RNA is inserted. When this plasmid is linearized and transcribed, the resulting RNA strand splices out the inserted sequence and circularizes it spontaneously by autocatalytic splicing, as seen schematically in FIG. 1(B).

The primary feature of the invention is a rearrangement of natural elements that code for a self splicing intron. An example of such self-splicing intron is the bacteriophage T4 td intron, but other self-splicing introns may also be used. In natural genes interrupted by introns, non-continuous exons are ligated together forming a "spliced" linear exon product. The intron may be excised in linear, lariat or other derivatives of these forms. Some introns may undergo further reactions such as a circularization reaction. However, such circularization reaction is not the same as the circularization of the current invention and should not be confused with the exon circularization reaction of this invention. The previously known intron circularization products retain large amounts of highly structured RNA as well as the autocatalytic activity of the intron, limiting its use in the design of RNA regulators of gene expression.

These problems are overcome by the method of this invention.

The rearrangement of the intron elements in the new plasmid according to the current invention divides an RNA within the intron, and joins parts of two exons, by placing the 3' portion of the gene upstream of the 5' portion of the gene. In the 5' to 3' direction, this creates a sequence consisting of the 3' half portion of the intron, the 3' splice site, the second exon (exon 2), the first exon (exon 1), the 5' splice site, and the 5' half portion of the intron. Upon RNA splicing, because there is one continuous exon composed of exon 2 plus exon 1 flanked by splice sites, the joining of the 5' and 3' splice sites circularizes the exon. This circularization is due to the RNA cyclase activity. The RNA cyclase activity is produced by the enzymatic splicing reactions of the intron RNA elements. The RNA cyclase acts as a kind of ribozyme and is therefore called RNA cyclase ribozyme.

During the rearrangement of the intron elements in the new plasmid, two segments of intron, the 3' half intron and 5' half intron are also produced by the RNA cyclase reaction. These segments retain the autocatalytic activity of the intron used to make the exon circular. The circular exon RNA products of the splicing reaction of the current invention do not retain this autocatalytic activity.

Further, in the method of the current invention, the existing exon sequence can be altered so that a desired sequence can be made circular. For example, plasmid pEFCΔNde contains, with exception of 100 nt of the td exon which is deleted, all nucleotides including a unique Nde1 site for easy insertion of a desired sequence to be rendered circular. By site directed mutagenesis it is possible to engineer a plasmid to contain any exon sequence as long as compensatory changes are made to satisfy the requirements of the so called P1 helix, part of which is encoded in the intron.

The current method possesses several new and advantageous features overcoming prior disadvantages encountered with other methods of creating circular RNA. As described above, two of the prior techniques involve the use of expensive protein enzymes and have the relatively low yield and poor reproducibility of the reactions. Because of these limitations, they require large amounts of linear starting material RNA. The third method uses the cyclization or circularization activity of group I introns. The problem with this approach is that the intron sequences themselves must remain as part of the RNA circle. Since the intron is a large (400 nucleotide) highly structured sequence with catalytic activities, the constraint of including such intron sequences severely limits the size and types of RNA sequences that can be made circular using the third technique. In addition, the remaining autocatalytic activity could hinder the function of circular RNAs made by this method, both in vitro and in vivo. There is currently no method available for controlled production of circular RNA in vivo.

In the current method, the enzyme that closes the RNA circle is synthesized as a ribozyme moiety of the transcript to be rendered circular. Such ribozyme moiety is released from the circle at the end of the reaction. Consequently, there is no need to supply the enzyme and no cost is incurred for the enzyme.

Second, the reaction gives an excellent yield. The reaction results typically in the molar yield of circles approaching those of the number of moles of transcripts synthesized.

Third, the reaction is accurate. Circular products produced by the current invention join at the precise phosphodiester bond created during splicing.

Fourth, no inseparable alternative products are formed. In some methods and under suboptimal reaction conditions, alternative products are formed. For some applications and uses the alternative circle products produced by other methods present problems due to heterogeneity at the ends of the linear RNA substrates used by the protein enzymes. This heterogeneity can lead to multiple different products which are very similar in size to the desired product but are not the same.

In contrast, if the alternative products are generated by the inaccurate circle formation in the current method, they are discrete and very differently sized. Consequently, the desired target product is easily distinguished from these alternative inaccurate circle products. This difference makes identification and purification of the desired product much easier.

Figure 1B:
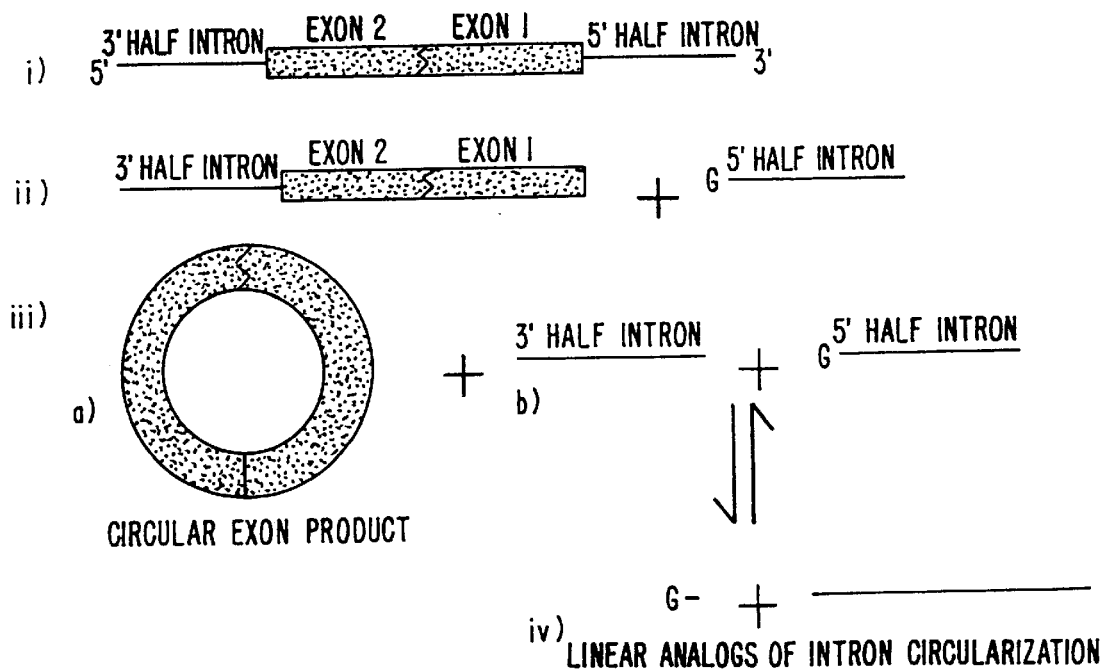

In the current invention, the td gene's group I intron was used to create a series of constructs that produce circular exon RNA upon group I splicing. This reaction is outlined in FIG. 1. FIG. 1(A) outlines the reaction involved in production of the normal spliced products from natural td gene as well as the intron cyclization reaction used by other methods. FIG. 1(B) outlines reactions involved in the production of circular splicing products from the rearranged inside out group I intron constructs.

In practice, a self-splicing group I intron from bacteriophage T4 td gene has been split and rearranged so that after transcription, a single internal exon is rendered circular by the group I splicing reaction. Transcripts derived from the construct have the 3' half of the intron at the 5' end, followed by the 3' splice site, the exon 2 and 1 sequences, followed by the 5' splice site and the 5' half of the intron (FIG. 1B). The 3' half and the 5' half of the intron associate to form the group I intron folded structure and splicing ensues, cyclizing the exon by the splicing reaction. In this manner, circular RNA of virtually any sequence can be obtained by cloning the desired sequence within or in place of the exon sequences of a plasmid, such as pEFCΔNde.

Other possible modifications of the current invention involve constructs using other group I introns besides T4 td, division of a group I intron in places other than the P6a region, division of group II introns, pre-mRNA introns, or use of RNA trans-splicing processes, as well as combinations of two different introns on separate transcripts. All of these modifications could be achieved essentially. in the same way as the current invention by creating a construct with a continuous exon to be rendered circular by an RNA splicing event. The methods for these modification are essentially the same as above, except for variations in vitro or in vivo splicing conditions. All these modifications are contemplated to be within the scope of this invention.

The method and plasmids of the current invention were tested by the inventors in both in vitro and in vivo conditions.

C. Production of Circular RNA Constructs in Vitro

Typically, to produce the circular RNA in vitro, the method requires three steps. The first step comprises inserting the nucleic acid sequence to be made circular into the exon sequence of the general use plasmid such as plasmid pRR1, using one or two of the exon polylinker sites, as described in Examples 11–13. Inserting the nucleic acid sequence is achieved by cloning, PCR, oligonucleotide directed mutagenesis or other techniques known in the art. Site directed mutagenesis techniques or deletion using restriction enzyme or other techniques known in the art are used to remove any undesired exon sequence derived from the polylinker as described in Example 16. Any changes connected with removal of undesired exon sequence and with inserting the desired sequence must be consistent with required exon contributions to the structures of P1, because changes in the few exon nucleotides directly adjacent to the 5' splice site influence group I splicing efficiency and accuracy. Changes in the exon contribution to P1 are accommodated by changing a few nucleotides in the intron contribution to P1, so that they pair with the desired alterations in the exon nucleotides adjacent to the splice site. This process restores the P1 pairing. By this step a new RNA cyclase ribozyme gene is produced which when transcribed produces a new circular RNA containing the desired sequences.

The second step comprises expression of plasmid by transformation, in vitro transcription, viral transcription, microinjection, electroporation, liposome mediated transformation or by other techniques known in the art. Preparation of RNA transcripts from the plasmid DNA, are described in Example 4. First, the DNA is cleaved with any restriction enzyme, such as for example SalI, which does not cut within the construct, to generate a transcription termination (runoff) site in the template. This site exists in the clone at the end of the 5' half of the intron. A general use construct, such as pEFCΔNde or pRR1, contains a T7 transcription promoter upstream of the 3' half of the intron at the 5' end of the transcript (see FIG. 2). Thus, using cut DNA from pEFCΔNde or pRR1 in a transcription reaction with T7 RNA polymerase and the four ribonucleoside triphosphates, RNA transcripts are initiated in the 3' half of the intron, proceed through the 3' splice site and into the exon sequences, then through the 5' splice site and the 5' half of the intron, terminating at the end of the 5' half of the intron at the restriction enzyme cut site.

The third step comprises self-splicing of the transcripts so that the 5' and 3' splice sites are joined creating the circles. With most derivative plasmids, such as pEFCΔNde or pRR1, this will occur to a large extent in the transcription reaction, where appropriate magnesium ions, temperature, and the required guanosine cofactor, such as GTP, are present as described in Example 4. Different constructs may vary in splicing efficiency under transcription conditions. Consequently, to obtain maximum splicing efficiency, it may be necessary to determine optimum temperature and magnesium concentrations for splicing. For constructs where this is desired, the transcription reaction can be followed by a separate splicing reaction under optimum conditions as described in Example 5.

In vitro transcription and splicing reactions were performed with constructs pEFC-ΔNde and pΔNAct(+) as described in Examples 4 and 5. The arrangement of these constructs, as described in examples 12 and 13, produced circular RNA upon in vitro transcription and group I splicing. The resulting RNA sequences were free from any group I intron sequence, as seen in FIG. 5.

Characterization of these transcription/splicing products were carried out by 2D gel electrophoresis according to Example 10. The pEFC-ΔNde and pΔNAct(+) constructs were transcribed according to Example 4 and group I autocatalytic splicing was performed according to Example 5. Two dimensional polyacrylamide gels were created according to Example 6. As seen in FIGS. 4 and 6, these transcripts show that in vitro circular RNA is produced by this method.

Figure 5A:
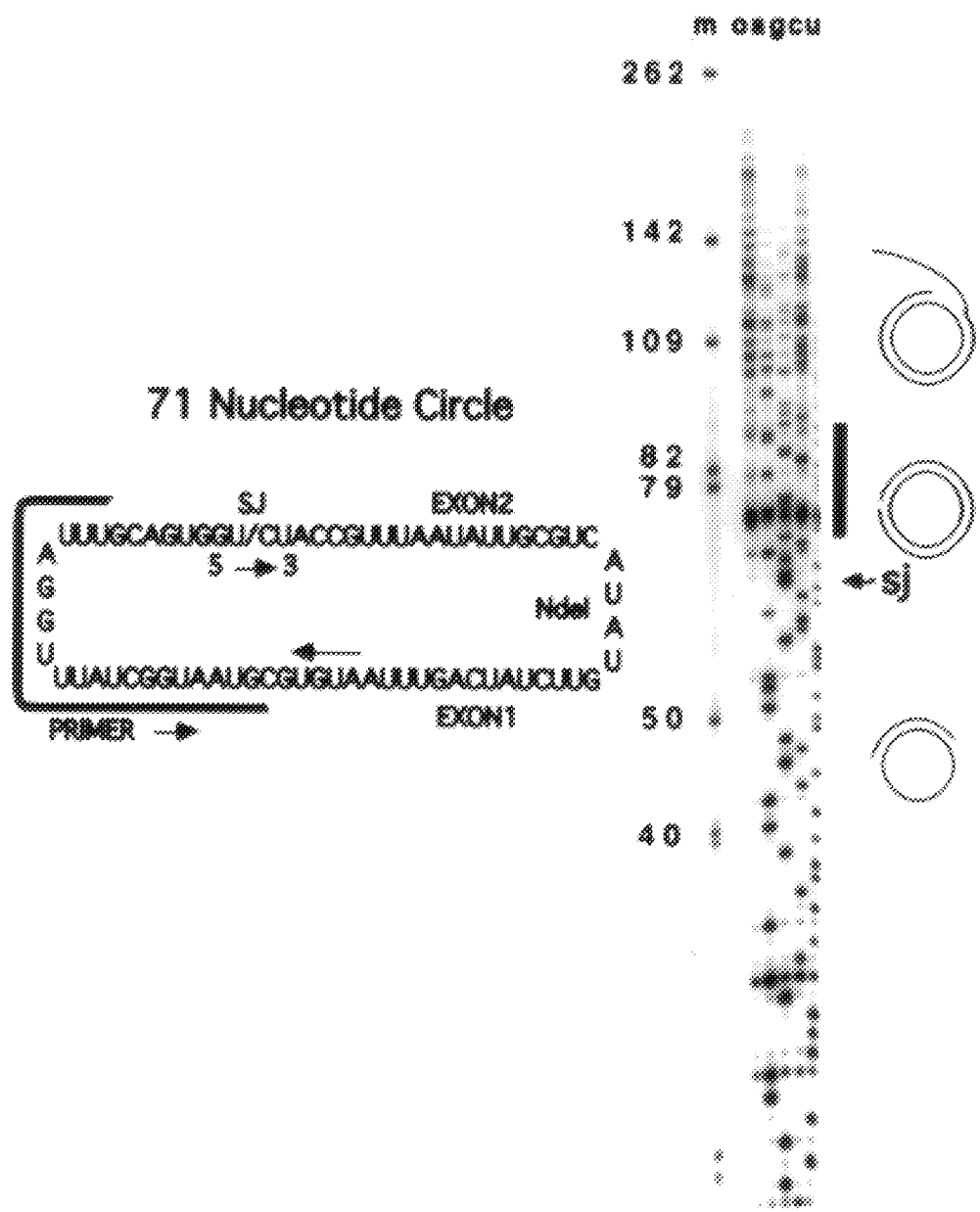
FIG. 5, panels A and B provide the dideoxynucleotide sequencing ladders of PEFCΔNde major circular in vitro transcription/splicing products wherein 5(A) is 71 nt circle (SEQ ID No: 2) and 5(B) is 100 nt circle (SEQ ID No: 3).
Figure 5B:
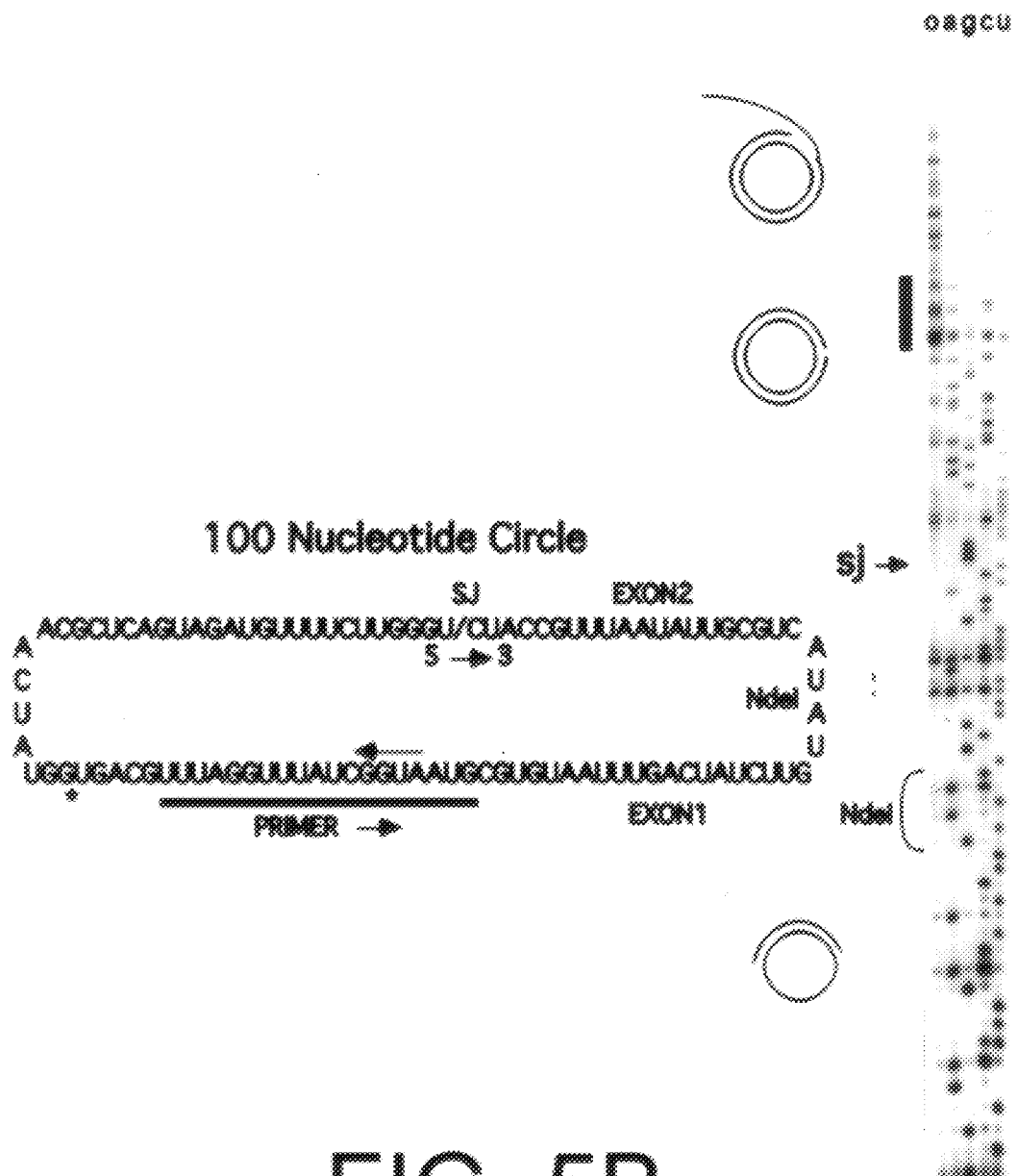

The two major circular products of pEFC-ΔNde were further characterized by RNA sequencing using reverse transcription in the presence of dideoxynucleotides as described in Example 4. Results are seen in FIGS. 5(A) and 5(B). These sequence ladders gave the expected sequences of the circular products using the correct 5' splice site and the alternative 5' splice site (*Genes Dev.,* 1:1028 (1987).

Production of Circular RNA Constructs in Vivo

The current invention also covers use of these constructs in vivo. The method for production of circular RNA in vivo requires four steps.

The first step, which is the almost same as the first step in vitro, described above, results in the creation of a plasmid-a gene for a new RNA cyclase ribozyme.

The second step involves placing the new RNA cyclase ribozyme gene into a vector containing the necessary elements for transcription and plasmid replication in the living organism to be used, using standard recombinant DNA techniques.

The third step requires that the expression vector containing the new RNA cyclase ribozyme gene be introduced into the desired organism.

The fourth step requires the maintenance of the organism under appropriate conditions to allow transcription of the expression vector. These conditions vary with different organism and different expression vectors.

The order of step one and step two can be reversed. In that case the general use prototype RNA cyclase ribozyme gene is first introduced into the expression vector, and then the new sequence to become circular is introduced at the appropriate position of the general use RNA cyclase ribozyme gene.

Figure 12A:
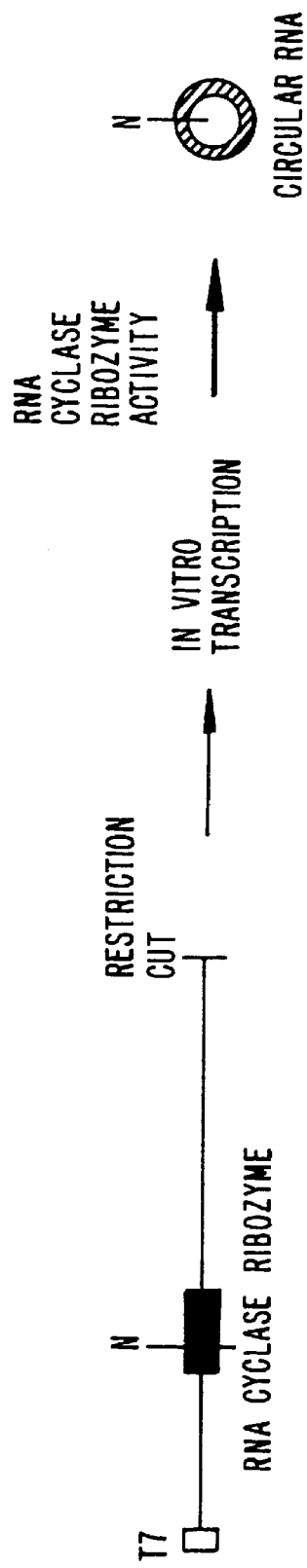
FIG. 12, panels A and B depict different functional contexts of RNA cyclase ribozyme in vitro and in vivo.

In order for RNA cyclase to be expressed in vivo in eukaryotes, special modifications such as mRNA capping and polyadenylation of the RNA cyclase RNA have to occur at a potentially sensitive site within the ribozyme. These modifications can be seen in FIGS. 2 and 12. In the in vitro application described above, RNA synthesis of the ribozyme is achieved by initiation of transcription by purified T7 RNA polymerase at the T7 promoter (FIG. 12A).

Figure 12B:
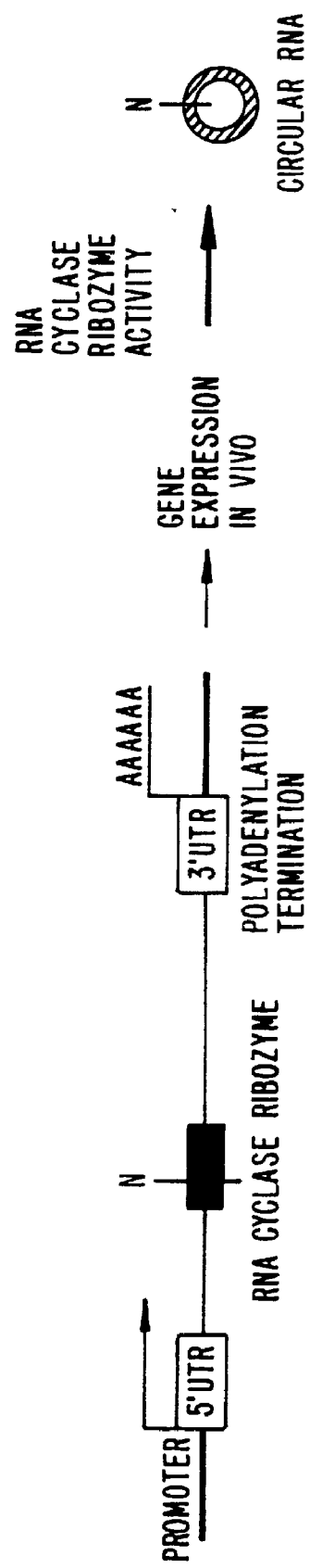

The efficient expression of genes in the wide variety of organisms potentially receptive to circular RNA technology depends on eukaryotic promoters and production of stable mRNA. The RNA cyclase ribozyme is efficiently transcribed by eukaryotic RNA polymerase II and more importantly the ribozyme tolerates the addition of 5' and 3' untranslated regions and poly(A) critical to the stable production of eukaryotic mRNA. The site of joining of these sequences to the ribozyme is known to be in the middle of the group I structural element called P6a. This site tolerates a phosphate backbone discontinuity and small additions of RNA. It was unknown, however, whether large additions of unjoined sequence needed for expression in vivo could be added to the ribozyme at this site while preserving RNA cyclase activity The expression of RNA cyclase ribozymes in vivo using these constructs shows that the RNA cyclase ribozyme gene sequences can be used as a "cassette", and can be inserted between elements necessary for efficient expression of eukaryotic genes without interfering with either efficient expression or RNA cyclase activity (FIG. 12B). Parallel constructs using promoters and polyadenylation sequences appropriate for other host organisms such as plants and animals including humans, should function in vivo. Specifically, the circular RNA would be produced in mammals and other vertebrates, nematodes, eukaryotic microbes, bacteria and cells in culture, as seen in FIG. 11, by inserting the RNA cyclase genes into an expression vector appropriate for expression in organism to be used. Examples of such vectors are a vector carrying Simian virus 40 replication elements using SV 40 promoter and intron, poly(A) site for mammals, an Agrobacterium Ti plasmid derivative carrying the selectable neo gene, and elements required for transfer into plants using Cauliflower Mosaic Virus 35S promoter for plants.

E. Production of Circular RNA In Vivo in Yeast

The method of producing circular RNA in vivo was demonstrated in yeast. Yeast strain IH1097 was transformed with plasmid constructs prepared according to the method described in Example 14 and 15. The RNA cyclase genes from the prototype pEFCΔNde and a derivative pΔNAct(+) were cloned into a yeast expression vector, according to Examples 14 and 15 to produce pΔN-Y(+) and pΔN-A(+)-G(+), respectively. The new constructs were introduced into yeast by transformation, and the efficient production of circular RNA in vivo was demonstrated. The circles were identical in size to those expected from accurate joining of the exon ends by the splicing reaction of the modified intron.

To test function in vivo, the RNA cyclase sequences were placed in a yeast expression vector carrying the galactose regulated GAL1 promoter and the CYC1 terminator from well characterized yeast genes. This construct, pΔN-Y(+), had an additional 70 nucleotides of GAL1 5' untranslated leader sequence as well as 155 nucleotides of CYC1 3' untranslated sequence. During transcription in vivo, these extra sequences and a poly(A) tail are added to the RNA cyclase ribozyme at the site of the phosphate backbone discontinuity at P6a' and P6a respectively. RNA cyclase ribozymes with these modifications were demonstrated to function in yeast as seen in FIGS. 8 and 9.

Depending on the precise sequences contained in the circle, the circles are stable. A new RNA cyclase construct containing part of the yeast actin gene including the 309 nucleotide actin intron was efficiently expressed. First, the actin intron was removed by the endogenous nuclear pre-mRNA splicing machinery, indicating that the T4 sequences dd not interfere with steps in gene expression associated with nuclear pre-mRNA splicing. Subsequently, the RNA cyclase rendered the spliced actin sequences circular, producing a stable circle of 245 nucleotides, 100 of which were derived from T4, and the remainder from actin mRNA (FIG. 9).

F. Production of Circular mRNA in *E. coli*

To test whether a circular mRNA could be produced by the invention, complementation of *E. coli* strain C600 thyA- was tested for growth without thymidine (td function) using pEFC. *E. coli* strain C600 thyA- was transformed to ampicillin resistance with pEFC, and as controls pEFC-ΔΔNde, pΔNT7Act(+), and pΔNT7Act(−) were used. on minimal media plates (no thymidine), only the strain transformed with PEFC was capable of growth. On minimal media plates with thymidine added to a final concentration of 50 micrograms/ml all transformants were capable of growth as seen in FIG. 10. This proves that group I splicing is taking place at the correct location to make the 3' end of td exon 1 continuous with the 5' end the td second exon so that the td can be translated into a functional protein product. Since the first exon and the AUG codon that signals the start of td translation on the primary transcript is downstream of second exon (FIG. 10) it is necessary for group I splicing to occur to produce a message that could be translated correctly. The complementation studies provide evidence that a circular RNA produced by the invention can act as a messenger-RNA and produce protein.

G. Detailed Description of Drawings In principle, RNA of many imaginable sequences can be rendered circular in high yield using the approach of the current invention. Such RNA does not contain intron sequences which would hinder the functionality of the produced RNA. The principle of the current invention is seen in FIG. 1.

FIG. 1, panels A and B are comparisons of normal group I splicing (A) and the RNA cyclase ribozyme (B) of the current invention.

FIG. 1(A) is a schematic illustration of natural group I splicing previously known, wherein a single continuous intron is inserted between exon 1 and exon 2. In the first step of splicing and under the normal and natural conditions, the intron folds into its secondary and tertiary structure and binds a free guanosine residue. The 3'—OH of the bound guanosine attacks the 5' splice site creating the intermediate products (ii). In the second step the 3'—OH of exon 1 attacks at the 3' splice site and thereby creates the final products (iii), two ligated exons and a free td intron. After the td intron is excised it can undergo further reactions such as the intron circularization reaction shown. However, the RNA circle created from this intron circularization reaction contains intron sequences. The circular intron products of the prior art seen in FIG. 1A should not be confused with the intron-free circular exon RNA products of RNA cyclase ribozymes seen in FIG. 1B.

FIG. 1(B) illustrates the splicing by the RNA cyclase ribozyme of the current invention. This reaction proceeds essentially in the same fashion as it does with the natural version of the T4 td gene except that because the order of the elements in the transcript is different, the products and reactants are different. The RNA transcript (i) in the 5' to 3' direction consists of the 3' half intron, the 3' splice site, exon 2, exon 1, the 5' splice site, and the 5' half of the intron. In the first step of splicing, the group I intron folds to form its correct secondary and tertiary structure and binds a free guanosine residue. In the case with the RNA cyclase ribozyme, however, the intron is not continuous, but contains the 5' and 3' ends of the transcript, whereas the exons are internal to the transcript. After the folding of the intron, the 3'—OH of the bound guanosine attacks the 5' splice site as it does in the natural version. This creates the two intermediates (ii), one containing 3' half intron connected to exons 2 plus 1, and the second containing the 5' half intron. In the second step (iii), the 3'—OH of exon 1 attacks the 3' splice site, joining the two ends of the continuous exon rendering it circular (circular exon product) and leaving behind two linear half introns (3' half intron+G-5' half intron), as seen in FIG. 1B (iii-b). The two half introns can undergo further reactions and create a linear analog of the intron circularization reaction (iv) with attached guanosine (G).

Resulting RNAs from the natural reaction and from the reaction of the current invention are different. The natural reaction produces a linear exon product containing exon 1 and exon 2 joined at the splice junction (iv). Rearranged group I splicing by RNA cyclase ribozymes according to the current invention produces an intron-free circular RNA product, consisting of only exon sequences (iii-a).

To produce the circular RNA of the current invention, the new plasmids were designed. These plasmids allow a unique splicing of RNA. FIG. 2, panels A, B, C, D, E and F depict plasmid constructs made according to Examples 10–16. FIG. 2 is a schematic representation of the plasmid constructs of the current invention. The following elements are represented by the following symbols: arrows represent transcription start sites; "N" marks Nde1 restriction sites; "3'ss" marks the 3' td splice site; "5'ss" marks the td 5' splice site; the thin lines represent the td half introns; bold lines represent the actin introns; empty boxes represent untranslated regions, lightly shaded boxes represent td exon 2 sequences, darkly shaded boxes represent td exon 1 sequences; and solid boxes represent actin exon sequence.

FIG. 2A represents the construct pEFC which has the tandem lac and phage T7 promoters. Downstream of the promoters in the 5' to 3' direction is the 3' half of the intron, the 3' splice site, exon 2, exon 1, the 5' splice site, and the 5' half of the intron. This construct is useful for production of circular RNA in vitro and in vivo in E. coli.

FIG. 2B is a schematic representation of the construct pEFCΔNde. This construct contains, in the 5' to 3' direction, the tandem lac and T7 promoters, the 3' half of the intron, a portion of exon 1, the Nde1 RNA cyclase cloning site created by a portion of exon 2, and the 5' half of the intron. This construct is useful for production of circular RNA in vitro and in vivo in E. coli, and as a prototype for creating new RNA cyclase ribozymes.

FIG. 2C is a schematic representation of the construct pΔNAct(+). This construct contains, in the 5' to 3' direction, the tandem lac and T7 promoters, the 3' half of the intron, the td 3' splice site, the deleted portion of td exon 2, partial actin exon 1, the actin 5' splice site, the actin intron, the actin 3' splice site, partial actin exon 2, the deleted portion of td exon 1, and the td 5' half intron. This construct is useful for production of circular RNA in vitro and in vivo in E. coli.

FIG. 2D is a schematic representation of pΔN-Y(+). This construct contains, in the 5' to 3' direction, the GAL1 promoter, the GAL 5' untranslated region, the 3' half of the td intron, a portion of td exon 1, the Nde1 RNA cyclase cloning site, a portion of td exon 2, the 5' half of the td intron, and the CYC1 3' untranslated region. This construct is useful for production of circular RNA in vivo in yeast.

FIG. 2E is a schematic representation of construct pΔN-A(+)-G(+). It contains, in the 5' to 3' direction, the GAL1 promoter, the 5' GAL1 untranslated region, the 3' half of the td intron, the td 3' splice site, a portion of td exon 2, partial actin exon 1, the actin intron 5' splice site, the actin intron, the actin 3' splice site, partial actin exon 2, the deleted portion of td exon 1, the td 5' half intron, and the CYC1 3' untranslated region. This construct is useful in production of circular RNA both in vitro and in vivo.

FIG. 2F is a schematic representation of pRR1. It contains, in the 5' to 3' direction, the tandem lac and T7 promoters, the 3' half of the intron and the 3' splice site, a polylinker sequence containing multiple restriction enzyme recognition sites, the 5' splice site and the 5' half intron. This construct is useful for producing circular RNA in vitro and in vivo in E. coli. It is also especially useful as a prototype for creating new RNA cyclase ribozymes.

Figure 3:
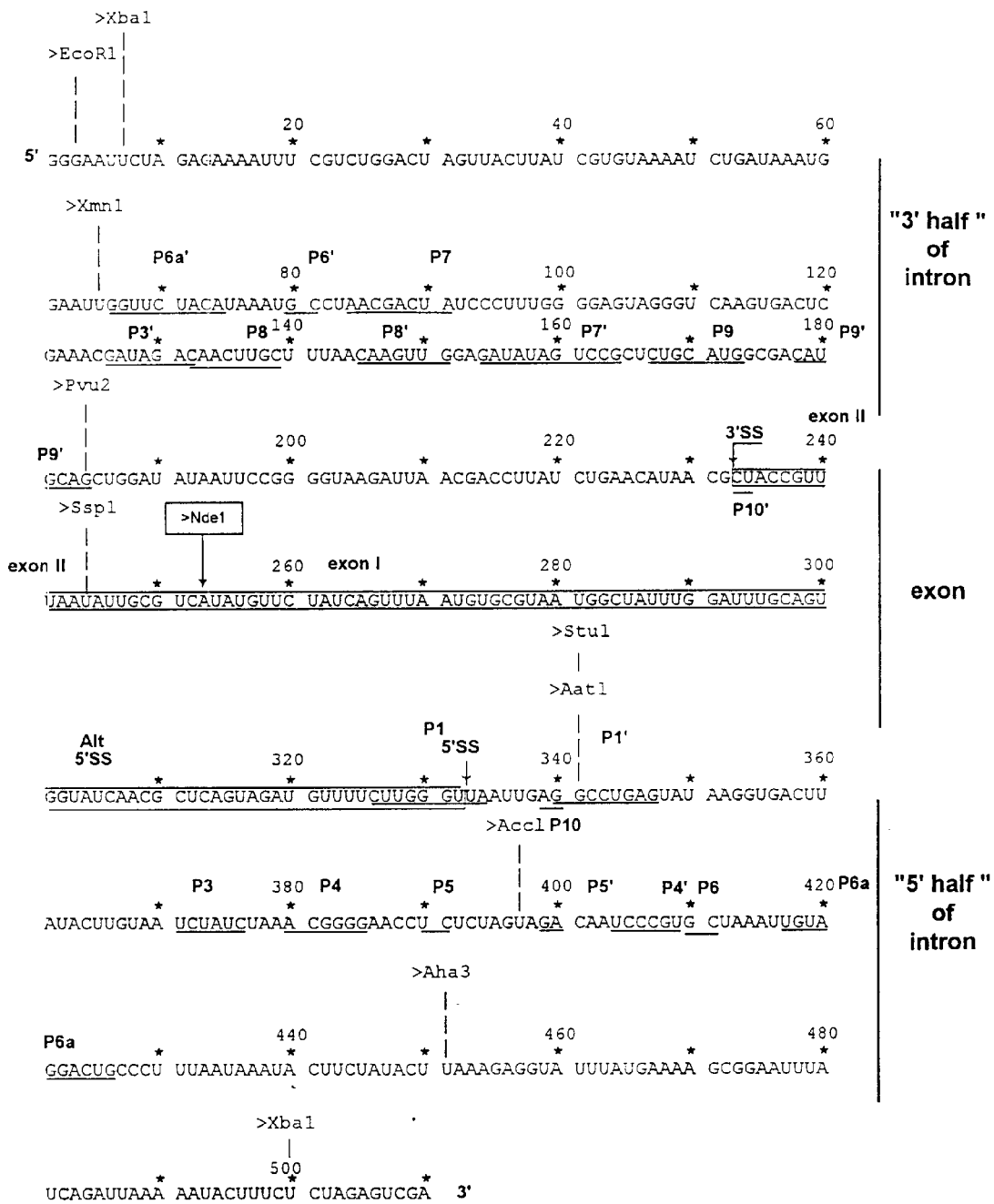
FIG. 3 is the sequence of the in vitro RNA transcript from PEFCΔNde linearized with SalI (SEQ ID No: 1).

In order to show that the spliced product had the desired sequence which was inserted into the construct, the sequence of the in vitro primary transcript was determined. FIG. 3 shows the sequence of the in vitro primary RNA transcript from the plasmid pEFCΔNde linearized with SalI and transcribed with T7 RNA polymerase(SEQ ID No: 1). Pairings required for group I intron function are labeled. The boxed sequence is the remaining td exon sequence; this is the sequence that is circularized along with any sequence inserted into the marked Nde1 site. The underlined P1 sequence is the only exon sequence that contributes to RNA cyclase ribozyme activity.

To show that the RNA cyclase ribozyme functions properly, 2D gel analysis of the RNA transcripts synthesized from the constructs was performed. FIG. 4 is a 2 dimensional polyacrylamide gel analysis of the in vitro transcription/splicing reactions of the construct pEFCΔNde linearized with SalI. Radioactive transcripts were produced as described as described in Example 4. The transcription products were incubated under optimal splicing conditions as described in Example 5. Two dimensional polyacrylamide gels were produced as described in Example 6.

Figure 4A:
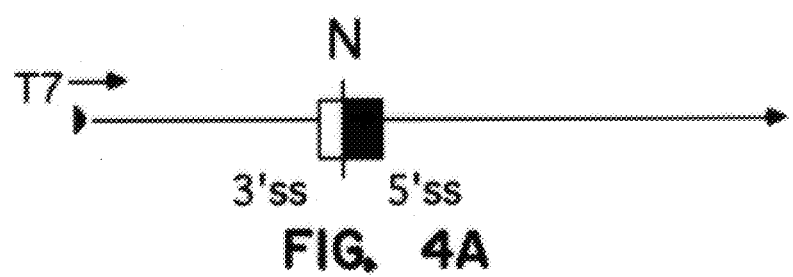
FIG. 4 panels A and B provide, respectively, the structure of and 2D gel analysis for PEFCΔNde transcription/splicing reactions.

FIG. 4(A) is a schematic representation of the pEFCΔNde transcript.

Figure 4B:
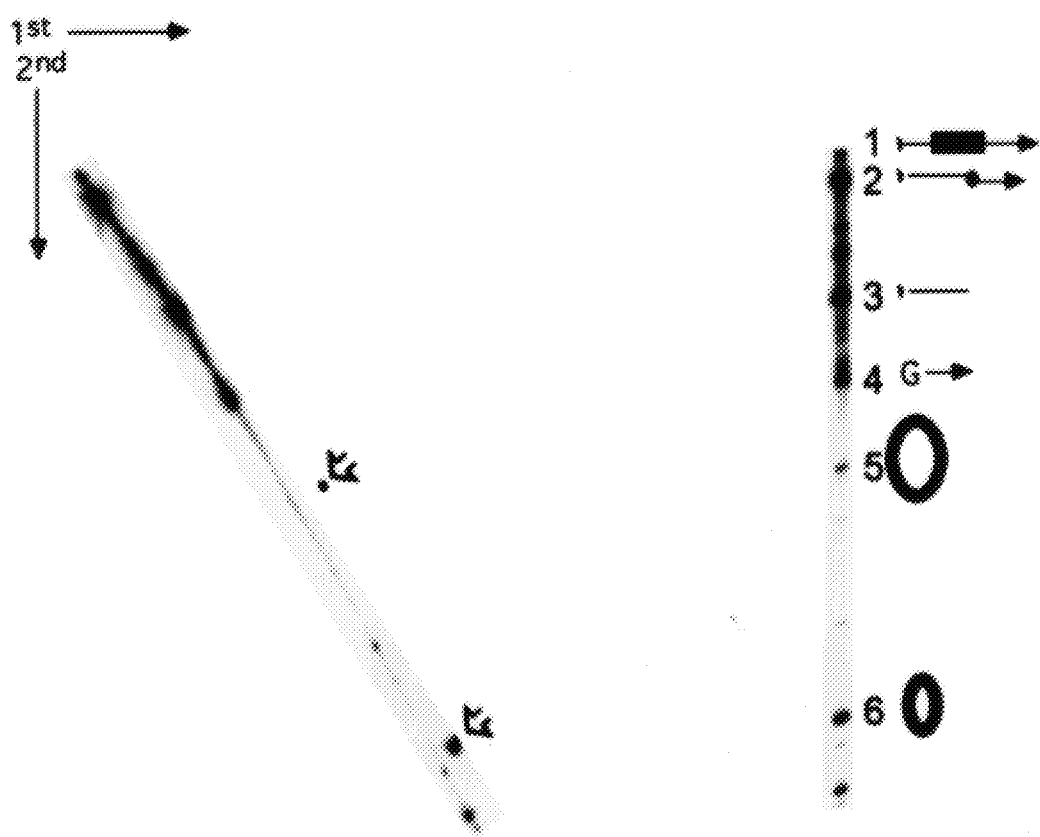

FIG. 4(B) is the 2D polyacrylamide gel of the transcription/splicing products of the pEFCΔNde construct. The first dimension was a 6% polyacrylamide (19:1) gel and the second dimension was a 8% polyacrylamide (19:1) gel. The major transcription products are schematically noted on the side next to the one dimensional markers using the same notation as in FIG. 1 (B). The first marked band (1) is the pEFCΔNde primary transcript. The second marked band (2) is the linear analog of the intron circularization reaction. The third marked band (3) is the 3' half of the intron. The fourth marked band (4) is the 5' half of the intron with the attached guanosine. The fifth marked band (5), also noted by an arrow on the two dimensional portion of the gel, is the 100 nt td exon circular RNA. This product was created by use of the correct splice sites. The bottom marked band (6) is the 71 nt td exon circle created by use of a previously identified 5' cryptic splice site described in Genes and Dev., 1:1028 (1987). Both these circular products (5) and (6) contain no intron sequences and are the circular products of the RNA cyclase ribozyme of the current invention.

To provide the evidence that the produced RNA is circular and not merely linear, the dideoxynucleotide sequencing was performed according to Example 7. Specifically, FIG. 5 shows the dideoxynucleotide sequencing ladders of the major circular in vitro RNA products derived by transcription of the construct pEFCΔNde linearized with SalI (Example 4) and incubation under splicing conditions (Example 5). The sequencing ladders were created as described in Example 7. The following elements are noted by symbols as follows: the solid bar identifies the primer sequence; "sj" identifies the splice junction; "Nde1" identifies the Nde1 restriction site; the circular line drawn around the circles next to the sequencing ladder represents the length of the reverse transcript at that region of the ladder; above the ladder each lane is marked with the complementary dideoxynucleotide added in the reaction. The "m" depicts pUC13/Sau3A markers and "0" represents control where no dideoxynucleotides were added.

FIG. 5(A) shows the sequence ladder of the 71 nt circle (SEQ ID No: 2) created by use of the 5' cryptic splice site. It is possible to read the sequence 1 nt past the end of the primer, through the splice junction, back into the primer sequence, and up to the splice junction a second time.

FIG. 5(B) shows the sequence ladder of the 100 nt circle (SEQ ID No: 2) created by the use of the correct splice sites. In this ladder it is possible to read the sequence 1 nt past the end of the primer, through the splice junction, into the primer sequence, and back into sequence already read. This Figure proves that the produced template RNAs are circular because they direct synthesis of reverse transcripts longer than the template chain length and these products are composed of direct reiterations of the sequence unit. Furthermore, the sequence unit matches the predictions of the RNA templates seen in FIG. 4A.

To provide the evidence that the RNA cyclase is functional when foreign sequence is inserted into it, 2D polyacrylamide gel analysis seen in FIG. 6 of the transcriptions/splicing reaction with pΔNAct(+) was performed.

FIG. 6 is a 2 dimensional polyacrylamide gel analysis of the in vitro transcription/splicing reactions of the construct pΔNAct(+) linearized with SalI. Radioactive transcripts were produced as described as described in Example 4. The transcription products were then incubated under optimal splicing conditions as described in Example 5. Two dimensional polyacrylamide gels were produced as described in Example 6.

FIG. 6(A) is a schematic representation of the in vitro RNA transcript from the pΔNAct(+) construct linearized with SalI. FIG. 6(B) is the 2D polyacrylamide gel of the transcription/splicing products of the construct pΔNAct(+). The first dimension was a 4% polyacrylamide (19:1) gel and the second dimension was a 5.5% polyacrylamide (19:1) gel. The major transcription/splicing products are schematically noted on the side in the same fashion as in FIG. 4(A). The first marked band is the circular RNA product created by the RNA cyclase ribozyme (1). The spot below the lower diagonal is a broken circle which became linear. Since this broken circle has the same size as a circle, it is used as internal marker for identifying the size, in this case 554 nt, of the circle. The second marked band (2) is the primary linear transcript. The third marked band (3) is the linear analog of the intron circularization reaction. The fourth band (4) is the 3' half of the td intron and the bottom marked band (5) is the 5' half of the td intron with the attached guanosine. FIG. 6(B) shows that the RNA cyclase ribozyme created during construction of pΔNAct(+) is functional: a completely foreign sequence inserted into the Nde1 RNA cyclase cloning site of pEFCΔNde is rendered circular.

Since the RNA cyclase ribozyme was shown to work in vitro, tests were performed to show that it also works in vivo.

Figure 7A:
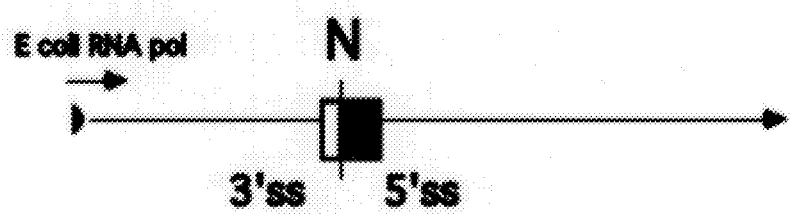
FIG. 7 Panels A and B provide, respectively, the structure of PEFCΔNde and a 2D Northern blot with total RNA from *E. coli* transformed with PEFCΔNde and probed with 32 P kinased td exon oligonucleotide.
Figure 7B:
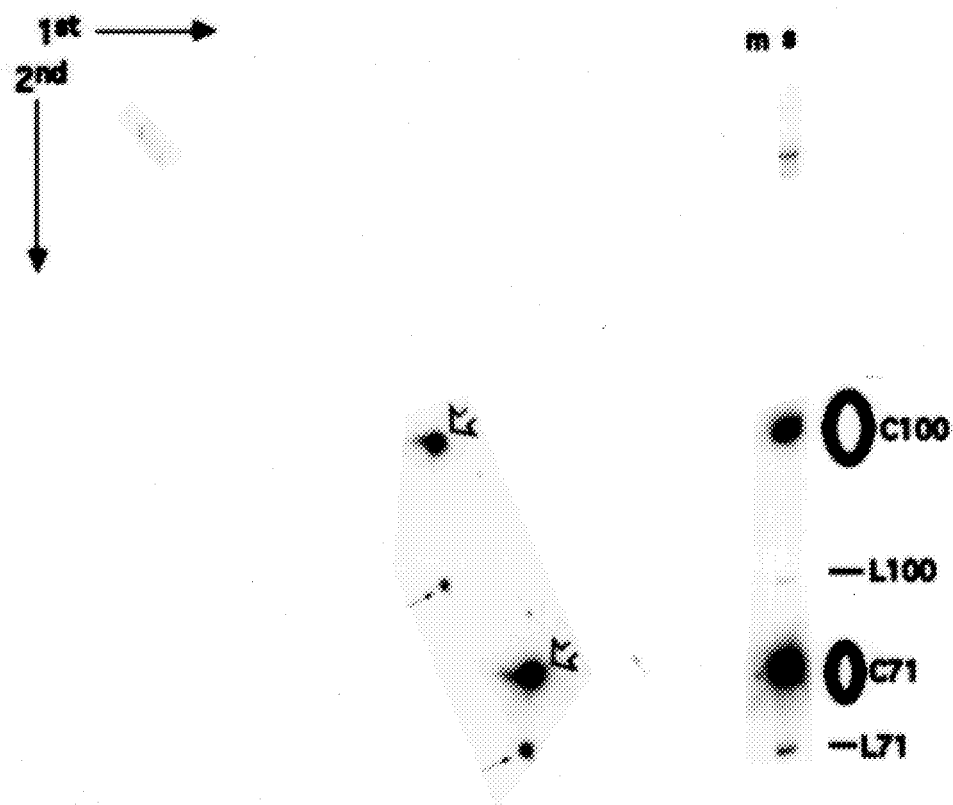

FIG. 7A is a schematic for the construct pΔN-A(+)-G(+). FIG. 7B shows 2D Northern blot with total RNA from E. coli transformed with pEFCΔNde and probed with kinased td exon oligonucleotide probe. The two dimensional Northern blots were created as described in Example 9. The first dimension was a 5.5% polyacrylamide (19:1) gel and the second dimension was a 8.0% polyacrylamide (19:1) gel. Two major circular products exist along with their linear analogs. These two circular products are the same sizes as the circular RNAs of 100 nt and 71 nt (sequenced in FIG. 5) created in vitro by the RNA cyclase ribozyme reaction of the current invention. The results seen in FIG. 7 prove that the RNA cyclase ribozyme functions in vivo in E. coli.

Similarly, FIG. 8 shows 2D Northern blot with total RNA from S. cerevisiae transformed with pΔN-Y(+) and hybridized with kinased td exon probe.

Figure 8A:
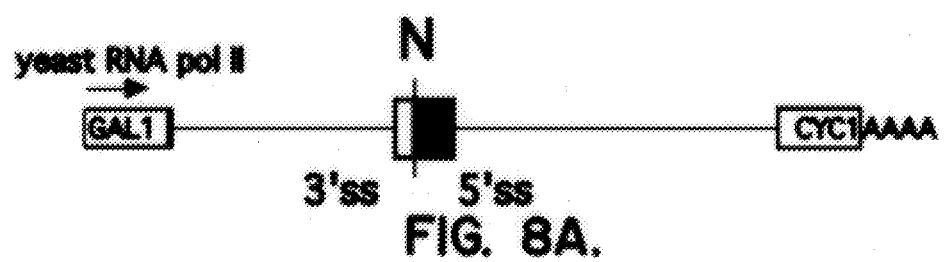
FIG. 8, panels A and B provide the structure of pΔN-Y (+) and a 2D Northern blot with total RNA from *S.cerevisiae* transformed with pΔN-Y(+) and probed with 32 P kinased td exon oligonucleotide probe.

FIG. 8(A) is a schematic representation of the primary pΔN-Y(+) transcript created in vivo in S. cerevisiae. This transcript contains, in addition to the RNA cyclase gene cassette of pEFCΔNde, a 5' GAL1 untranslated region, a 3' CYC1 untranslated region, as well as a poly(A) tail.

Figure 8B:
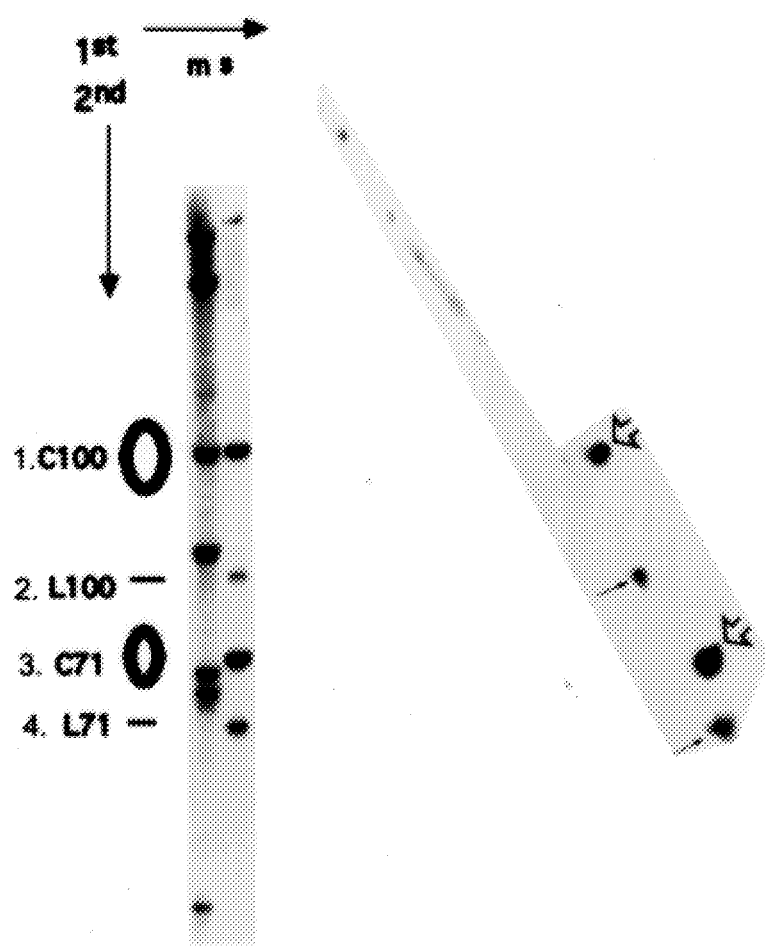

FIG. 8(B) is a two dimensional Northern blot with total RNA from S. cerevisiae transformed with pΔN-Y(+) and kinased td exon probe. This two dimensional blot was created as described in Example 9. The first dimension was a 6% polyacrylamide (19:1) gel and the second dimension was a 8% polyacrylamide (19:1) gel. Two major circular products are seen on this blot, marked by the large arrows, along with their linear analogs, marked by the small arrows. These two circular products are the same as the circular RNAs of 100 nt (1) and 71 nt (3) (sequenced in FIG. 5) created by the invention in vitro. Their linear analogs are L100 (2) and L71 (4).

FIG. 8 provides evidence that the RNA cyclase ribozyme functions in vivo in yeast under the control of RNA polymerase II. Further, it shows that the RNA cyclase ribozyme can tolerate the additions of 5' and 3' untranslated regions and a poly(A) tail required for efficient expression in eukaryotes. Prior to the results obtained in the experiment illustrated in FIG. 8(B), it was unknown whether large addition of unjoined sequence could be added to the ribozyme at these sites while preserving RNA cyclase activity.

Furthermore, the FIG. 8 shows that the RNA cyclase gene cassette does not possess cryptic transcription termination signals that would interfere with expression. The above results prove that the RNA cyclase ribozyme genes created using the prototype plasmid can be transferred to the context of a eukaryotic expression vector. In these contexts the RNA cyclase ribozymes can function in eukaryotic cells.

To show that an RNA cyclase ribozyme can create circular RNA containing foreign sequence in vivo, and that RNA cyclase ribozyme synthesis and function is compatible with nuclear pre-mRNA splicing in eukaryotes, the expression of circular RNA from pΔN-A(+)-G(+) was tested.

FIG. 9 shows 2D Northern blot with total S. cerevisiae transformed with p N-A(+)-G(+) and kinased td exon probe.

Figure 9A:
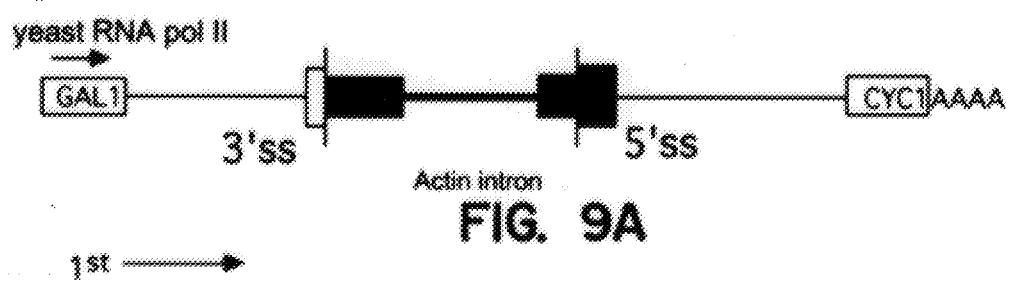
FIG. 9, panels A and B provide the structure of pΔN-A (+)-G(+) and a 2D Northern blot with total RNA from *S. cerevisiae* transformed with pΔN-A(+)-G(+) and probed with 32 P kinased td exon oligonucleotide probe.
Figure 9B:
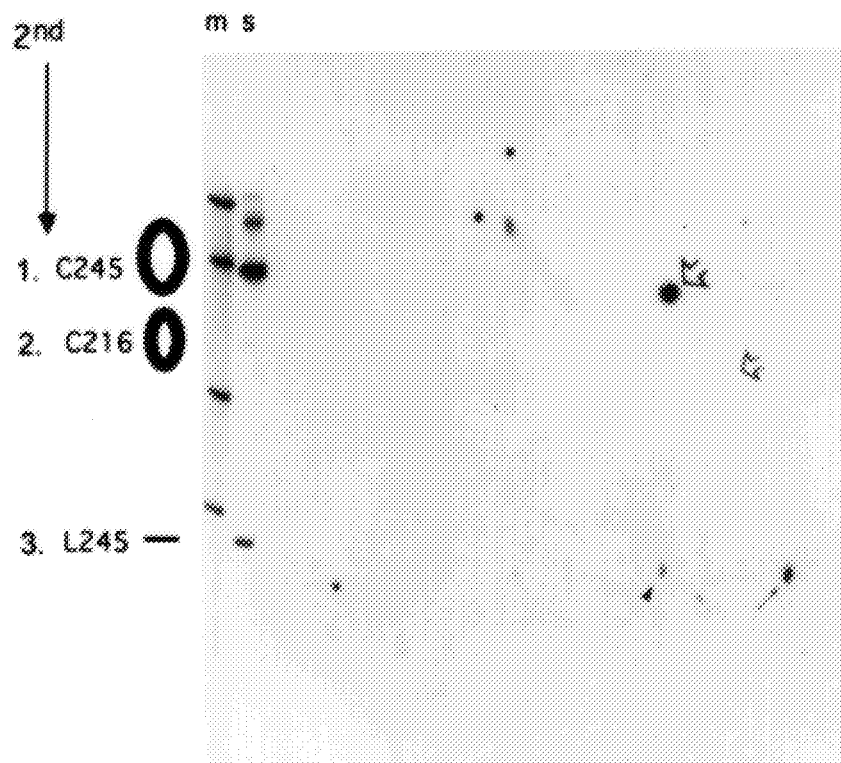

FIG. 9(A) is a schematic representation of the primary p N-A(+)-G(+) transcript created in vivo in S. cerevisiae. This transcript contains, in addition to the RNA cyclase ribozyme with the actin insert of pΔNAct(+), a 5' GAL1 untranslated region, a 3' CYC1 untranslated region, as well as a poly(A) tail. FIG. 9(B) is a two dimensional Northern blot with total RNA from S. cerevisiae transformed with pΔN-A(+)-G(+) and probed with kinased td exon oligonucleotide. This two dimensional blot was created as described in Example 9. The first dimension was a 4.5% polyacrylamide (19:1) gel and the second dimension was a 6% polyacrylamide (19:1) gel. One major circular product (1) and one minor circular product (2) are seen on this blot, marked by the large arrows, along with the linear analog of the major one (3), marked by the small arrow. The two circular products are the 245 nt and 216 nt circles created by the actin intron being spliced out of the transcript before the circularization reaction by the RNA cyclase ribozyme takes place. As before, the circles of different sizes arise from the use of the correct and the cryptic 5' splice sites, with the larger circle resulting from use of the correct splice site and the smaller circle resulting from the use of the cryptic 5' splice site.

The FIG. 9 proves that the RNA cyclase accommodates the insertion of extra sequence into the Nde1 RNA cyclase cloning site and will function to render the RNA circular within a eukaryotic cell. In addition, the existence of a nuclear pre-mRNA introns in the RNA cyclase ribozyme gene does not block function of the RNA cyclase.

To show whether the RNA cyclase ribozyme can be used to create a functional messenger RNA the ability of pEFC to code for td protein in vivo was tested.

FIG. 10 illustrates complementation of thy(−) E. coli with construct pEFC.

Figure 10A:
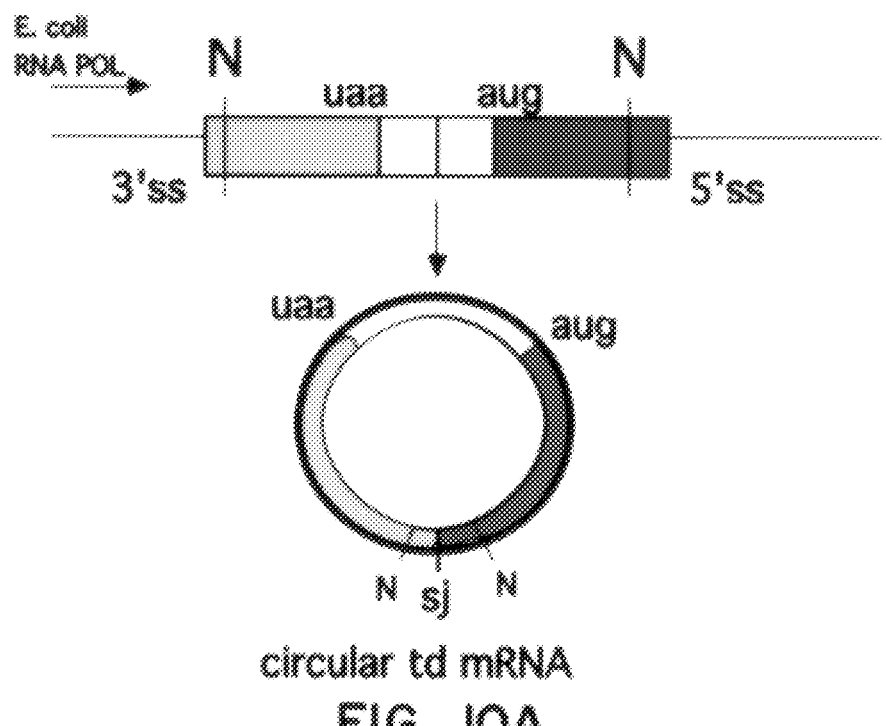
FIG. 10, panels A and B show complementation of thyA(-) *E.coli* with construct PEFC.

FIG. 10(A) is the schematic representation of the primary pEFC transcript. The primary transcript does not have a continuous reading frame through the two exons, thus RNA cyclase ribozyme activity is necessary to create functional td gene product mRNA. The circular product of the RNA cyclase group I splicing event is shown below the primary transcript. This circular message has a continuous translational reading frame through the two exons and if translated it could form a functional td gene product. Functional td product allows thy(−) E. coli to grow on medium lacking thymidine.

Figure 10B:
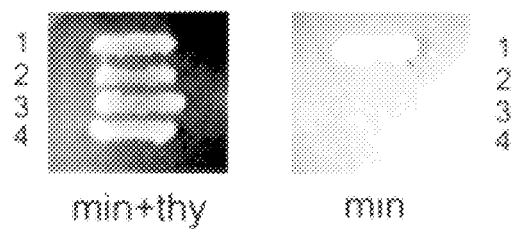

FIG. 10(B) show the results of the complementation experiment. The plates were streaked with E. coli strain C600 thy(−) (thymidine deficient) transformed with the following constructs: PEFC (1), pEFCΔNde (2), pΔNAct(+) (3), and pΔNAct(−) (4). The plate on the left is minimal media, 100 micrograms/ml ampicillin, and 50 micrograms/ml thymidine. The plate on the right is the same except that it contains no thymidine. As expected all the constructs are capable of growth on the plate with thymidine. However, on the plate lacking thymidine only the strain transformed with pEFC was capable of growth. This proves that the RNA cyclase ribozyme produces a message that is translated to produce td protein.

The general method for creating circular RNA in mammalian and plant cells is illustrated in FIG. 11. The FIG. 11 shows, in diagram, how to create circular RNA in animal and plant cells with the current invention.

Two steps of the method precedes introduction of the vector into the organism where the circular RNA is to be produced. First, plasmid is constructed with exon sequences to contain DNA sequence desired to become circular RNA and then DNA segment is recovered and introduced into expression vector appropriate for expression in organism to be used. If the circular RNA is to be produced in animals, exemplary vector carrying Simian Virus 40 replication elements SV40 promoter is used.

If the circular RNA is to be produced in plants, exemplary Agrobacterium Ti plasmid derivative carrying the selectable neo gene and elements required for transfer into plants and Cauliflower Mosaic Virus 35S promoter is used.

Expression vectors have selectable markers, elements required for introduction and/or maintenance of DNA in the cell and the proper elements for host expression of RNA, such as promoters, introns, polyadenylation, and termination signals. Xba is used to illustrate other standard cloning techniques. The order of step 1 and step 2 is not obligate; it could be reversed.

FIG. 12 depicts different functional contexts of RNA cyclase ribozyme in vitro and in vivo.

FIG. 12 illustrates different functional contexts of RNA cyclase ribozyme. FIG. 12 shows (a) in vitro, (b) in vivo RNA cyclase ribozymes. N denotes the convenient Nde I site for insertion of sequences to be included in the circle. The black box represents 100 nucleotides of T4 td exon sequences contained in pEFC Δ A Nde.

Figure 13A:
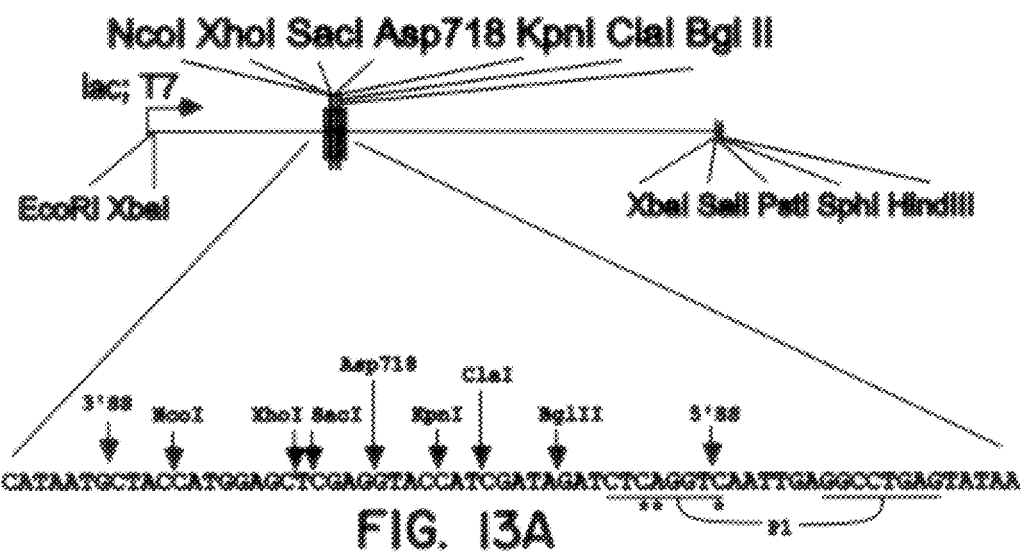
FIG. 13, panels A, B and C depict the structure and function of a general use plasmid of the invention that can be used to synthesize a prototype RNA cyclase ribozyme containing a polylinker in place of td exon sequences.
Figure 13B:
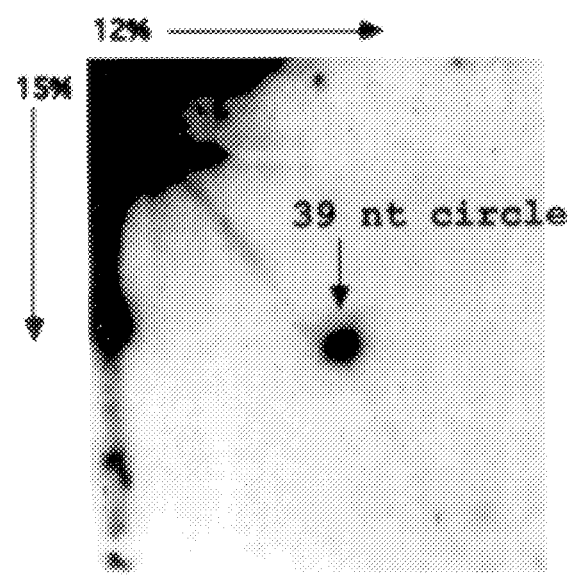
Figure 13C:
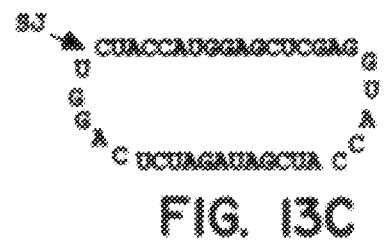

To show that the residual td exon sequence can be deleted and replaced with foreign sequence, and to provide a more convenient plasmid for the design of circular RNAs of many imaginable sequences the plasmid pRR1 was created as seen in FIG. 13. As described in Example 16, the td exon sequences remaining in pEFCΔNde were deleted and replaced with a "polylinker" sequence unrelated to the td exon (FIG. 13A). The sequence of this polylinker exon (SEQ ID No: 4) is shown in the middle of FIG. 13. The splice sites and the positions of unique restriction sites are indicated. The advantages of the polylinker sequence is that the restriction enzyme recognition sites can be used for introduction of a DNA sequence in the design of new RNA cyclase ribozyme genes. New sequences can easily be introduced between the splice sites, as described in the method and examples, and after transcription into RNA will become circular through the action of the RNA cyclase ribozyme elements on either site. For more demanding applications where the residual polylinker must be removed, oligonucleotide directed mutagenesis techniques (Example 16) can be used to "rewrite" the sequences near the splice sites. Nucleotides within P1 have been modified as well (asterisks), demonstrating that this sequence can be adjusted if desired. As shown in FIG. 13B, upon in vitro transcription (Example 4) and two dimensional denaturing gel electrophoresis described in Example 6 where the first dimension is 12% acrylamide and the second dimension is 15% acrylamide, pRR1 derived RNA cyclase ribozyme efficiently generated the predicted 39 nucleotide circular polylinker RNA. The sequence of the 39 nt circular polylinker RNA (SEQ ID No: 5) is seen in FIG. 13C. SJ indicates splice junction. This proves that exon sequences including P1 can be replaced by desired sequences and provides a general use form and a modifiable prototype for the invention.

UTILITY

The current invention provides efficient production of circular RNA in vitro and in vivo. Circular RNA of this invention is useful in the design of stable forms of RNA used as regulators of gene expression, for the design of circular mRNAs and for structure and function studies of RNA. The method of this invention is useful for molecular biology experimentation. Circular RNA is useful as a design element which will improve the stability and activity or efficacy of antisense or ribozyme gene regulation technologies. Additionally, the method is useful as mRNA to direct the synthesis of very long multiply repeating protein chains in vivo. Recently, (Science, 268:415 (1995)), it has been shown that circular RNA synthesized by the previously known methods described in Science, 256:992 (1992) was able to produce mRNA directing synthesis of these long proteins in vitro. That method is not able to produce circular mRNA in vivo.

A plasmid construct of this invention can in principle, upon transcription and autocatalytic group I splicing, turn almost any imaginable RNA sequence into a circle. The splicing reaction proceeds very efficiently with RNA transcribed from the prototype plasmids pEFC-ΔNde, pRR1 and derived constructs in vitro and in vivo.

The use of this new plasmid for making circular RNA has considerable advantages over existing techniques. Some of these techniques require the use of expensive proteins and have low yields. Another current technique results in retention of long intron sequences that severely limit the types of inserts that can be used. Also, in all prior attempts to produce circular RNA in vivo, the catalytic activity of the intron sequences is retained, and can interfere with further use of circular RNA derived from them. The system described here avoids these problems, and would become the method of choice for anyone constructing circular RNA.

Example 1

E. coli Strains and Media Preparation

This example illustrates preparation and growth of E. coli strains and media.

E. coli strain DH5α is endA1, hsdR17, supE44, thi-1, recA1, gyrA(Nalr), relA1, Δ(lacZYA-argf)U169, phi80lacΔ (lacZ)M15). DH5α thyA is DH5α with a thy A: kanR deletion/insertion. Strain CJ236 is F' cat (Cmr), dut, ungl, thi-1, relA1, spoT1, mcrA.

Media: E. coli strain DH5α and CJ236 were grown in LB, E. coli strain DH5α thyA was grown in M9 plus 50 micrograms/ml thymidine, according to Current Protocols in Molecular Biology, Units 1.1 and 1.7, Ausubel et al Eds., Publishing Associates and Wiley Interscience (1989) as supplemented through May 19, 1993.

Transformation of E. coli was accomplished according to Current Protocols in Molecular Biology, (ibid).

Example 2

Yeast Strains and Media Preparation

This example illustrates preparation and growth of yeast strains.

Yeast strain 1H1097 is MATa1, GAL2, ura3-52, leu2-3, 112, trp1, pep4-3, prb1, prc1. Yeast strain IHI097 was grown in SC glycerol-uracil according to Current Protocols in Molecular Biology, Unit 13.1, (ibid). Gal dependent transcription was induced by addition of one tenth volume of 30% galactose when the cells reached an O.D-600 from 0.1 to 0.2.

Transformation of yeast was accomplished according to Current Protocols in Molecular Biology, (ibid).

Example 3

Preparation of Primers and Probes

This example illustrates preparation of primers and probes utilized in the current invention.

The td exon oligonucleotide (5'-AAATCCAAATAGCCATTAC-3') (SEQ ID No: 6) is specific for both the correct and alternate td exon products. This oligonucleotide was used as a primer for reverse transcription products of pEFCΔNde. It was labeled at its 5' end with [$^{32}$P]phosphate using [$\gamma^{32}$P]rATP and polynucleotide kinase.

Example 4

Method for in vitro Transcription.

The following method was used for in vitro transcription.

Plasmid DNA from alkaline lysis preparations of E. coli were purified by CsCl gradient ultracentrifugation according to Current Protocols in Molecular Biology, (ibid). DNA was then linearized by cutting with restriction enzyme Sal 1 in the case of pEFCΔNde and pΔNAct(+). The plasmid template DNA (0.5 to 1 microgram) was incubated at 37° C. for 1 hour with 10 units of T7 RNA polymerase obtained from New England Bio Labs (Beverly, Mass), 20 microcuries of [α-$^{32}$p] UTP, 20 units RNase obtained from Promega (Madison, Wis.), in 4 mM ATP, 4 mM GTP, 4 mM CTP, 100 micromolar UTP, 40 mM Tris-Cl (pH 8.0), 16 mM MgCl2, 5 mM dithiothreitol, 1 mM spermidine and 0.01%(v/v) Triton X-100 in a total volume of 10 microliters for radioactive transcriptions.

Nonradioactive transcriptions were performed by the same method except 4 mM UTP, 22 mM MgCl2 and no [α-$^{32}$p] UTP was used. Constructs pEFCΔNde and pΔNAct (+) were shown to generate RNA cyclase ribozymes that produce the desired circular RNA as seen in FIGS. 4 and 6.

Example 5

Methods for in vitro Splicing

This example provides a protocol for in vitro splicing (RNA cyclase ribozyme activity) of pEFCαNde, or pαNAct (+) RNA transcripts.

Transcripts were created as described above in Example 4. These transcripts were purified by adding 350 microliters DEPC treated H$_2$O (DEPC treatment of water to remove ribonucleases is described in Current Protocols in Molecular Biology, (ibid) 40 microliters 3M sodium acetate, and 400 microliters phenol:chloroform:isoamyl alcohol (25:24:1). This mixture was vortexed, spun in a microfuge, and the upper aqueous layer transferred to a silanized microfuge tube as described in Current Protocols in Molecular Biology, ibid. One ml of 95% ethanol was added and mixture was incubated on dry ice for approximately 5 minutes to precipitate nucleic acids. The mixture was spun in a microfuge for 5–10 minutes, the supernate was discarded, and 1.5 ml of 70% ethanol was added. The mixture was spun in a microfuge for approximately 15 seconds, the supernate was discarded, and the pellet was dried under vacuum. The pellet was resuspended in 49 microliters DEPC treated H$_2$O.

The splicing reaction was performed by adding 50 microliters 80 mM Tris-Cl (pH 8.0), 6 mM MgCl$_2$, 10 mM dithiothreitol, 2 mM spermidine, and 0.02% (v/v) Triton X-100 and 1 microliter 1 mM rGTP. The mixture was incubated at 55° C. for approximately 30 minutes. Template DNA was removed by adding 1 unit RNase free DNase (Promega, Madison, WI) and incubating at 37° C. for an additional 20 minutes. Splicing reactions were purified by adding 260 microliters DEPC treated H$_2$O as described in *Current Protocols in Molecular Biology*, (ibid), 40 microliters 3M sodium acetate, and 400 microliters phenol:chloroform:isoamyl alcohol (25:24:1). This mixture was vortexed, spun in a microfuge, and the upper aqueous layer transferred to a silanized microfuge tube. One milliliter of 95% ethanol was added and the mixture was incubated on dry ice for approximately 5 minutes to precipitate RNA. The mixture was spun in a microfuge for 5–10 minutes, the supernate was discarded, and 1.5 ml of 70% ethanol was added. The mixture was spun in a microfuge for approximately 15 seconds, the supernate was discarded, and the pellet was dried in a speed vacuum. The pellet was resuspended in the desired volume of DEPC treated ddH$_2$O.

Example 6
Two Dimensional Gel Electrophoresis Method

This example illustrates two dimensional (2D) gel electrophoresis method used in analyzing the current invention.

First, an RNA sample was loaded onto one lane on a low percentage polyacrylamide gel prepared as described in *Current Protocols in Molecular Biology*, ibid, section 7.6.1, and electrophoresis was carried out. The lane from the first dimension gel was cut out as a narrow strip of gel, laid across the top of another set of glass plates, and a higher percentage polyacrylamide gel was then cast around it. A small gel comb containing one or two teeth was placed in the second dimension gel on one or both sides of the first dimension gel strip, in order that marker samples can be loaded in the second dimension. The second dimension was run with a portion of the original RNA sample and pUC13/Sau3A as one dimensional markers. The gel was dried and autoradiographed. Two dimensional gel electrophoresis separated linear molecules from non-linear molecules. The linear molecules formed a lower diagonal. Non-linear molecules, because of their relatively slower migration in higher percentage gels compared to linear molecules of the same length, formed an upper diagonal. If a circular molecule was nicked between the first and second dimension, it migrated as a circle in the first dimension and as a linear in the second dimension. This position is directly below the spot where the circle migrates and to the left of the spot on the linear diagonal where a linear of the same length migrates, below the lower diagonal. These nicked circles provide a useful means of determining the linear length of the circles in question. Higher percentages of acrylamide were necessary to distinguish smaller circles from linears, and resolution was less apparent for circles smaller than 35–40 nucleotides.

Example 7
Method Used for Reverse Transcription and RNA Sequencing

This example illustrates methods used for reverse transcription and RNA sequencing.

Transcription/splicing products, produced as described in Examples 4 and 5 were purified by electrophoresis on 7.5M urea 6% polyacrylamide (19:1) gels. RNA bands were cut out and eluted overnight in 400 microliters of elution buffer consisting of 0.3M sodium acetate pH 5.2, 5mM EDTA, and 0.5% SDS at 4° C. The liquid surrounding the gel piece was removed and extracted once with phenol/chloroform/isoamyl alcohol (25/24/1;v/v/v). RNA was precipitated with 95% ethanol, resuspended in water and diluted to approximately 10 picomolar solution.

Five identical reactions were set up each containing 1 microliter of approximately 10 pM gel purified RNA, 2.5 pg of end-labeled oligonucleotide, 1 microliter of 10×RT buffer consisting of 1.25M Tris-HCl pH 8.3, 175 mM KCl were mixed and water was added up to 13 microliter. The mixture was incubated at 65° C. for 5 min and then at 42° C. for 30 min. Then 1 microliter of water or a single ddNTPs stock was added to each single above reaction as follows: ddATP or ddGTP, 0.75 mM each, ddCTP, 1 mM; ddTTP and 1.5 mM. To each reaction, 1 microliter 10×RT buffer, 1 microliter of 0.1M dithiothreitol, 1 microliter of 100 MM MgCl$_2$, 1 microliter of 2.5 mM each dNTP, 0.5 microliters of 1 mg/ml actinomycin D, and 0.5 microliter (20 units/microliter) of AMV reverse transcriptase obtained from Life Sciences (St. Petersburg, Florida) was added and the mixture was incubated at 42° C. for 30 min. 10 microliters of RNase solution containing 1 mg/ml of RNase A, 30 mM EDTA, and 0.6M sodium acetate (pH 5.2), was added and incubated for 5 min at 42° C. Then 10 microliters of a proteinase K solution (1 mg/ml of proteinase K, 0.2% SDS, and 0.6M sodium acetate) was added and samples were incubated at 42° C. for 10 min. Samples were ethanol precipitated and resuspended in 1 microliter of 20 micrograms/ml proteinase K, 25 mM EDTA and 2 microliters of formamide loading dyes containing 98% formamide, 0.1×TBE, 0.05% xylene cyanol, and 0.05% bromophenol blue, and electrophoresed on 7.5M urea 6% or on 8% polyacrylamide (19:1) gels. The RNA sequencing ladders shown in FIG. 5 provide evidence that the gel purified bands used as templates are the circular RNA exon products assigned in FIG. 4.

Example 8
Methods for RNA Extraction from *E. coli* and Yeast

This example illustrates methods used for extraction of RNA from *E. coli* and yeast.

*E. coli* bacterial strains were grown in LB with 100 micrograms/ml ampicillin until mid-log phase at 37° C. After 1 hour cells were pelleted by centrifugation. Total cellular RNA was extracted essentially as described previously in *Genes and Dev.*, 4:2132 (1990) for yeast. Cell pellets were resuspended in 0.5 ml of AK buffer. AK buffer contains 1 gram of triisopropylnaphthalene sulfonic acid, 6 grams sodium chloride, and 6 ml of phenol per 100 ml. Hot (65° C.) phenol (0.5 ml) was added, and the mixture was vortexed on high speed for 5 sec, and incubated at 65° C. for 30 min during which time it was vortexed twice more for 10 sec each. The mixture was incubated on ice for 5 min and spun in a microcentrifuge for 10 min. The aqueous phase was removed and extracted once with phenol/chloroform/isoamyl alcohol (25:24:1) and once with chloroform. Sodium acetate having pH 5.2 was then added to a final concentration of 0.3M and the RNA was precipitated by the addition of 2.5 volumes of 95% ethanol. The pellet was resuspended in 300 microliters of water. The RNA was used for Northern Blot analysis described in Example 10.

Yeast strains were grown in 50 ml of SC glycerol (-) uracil to an O.D.600 between 0.1 and 0.2. To induce transcription, 5 ml of 30% galactose was added, and cells were grown to an O.D.600 between 0.3 and 0.4 before harvesting by centrifugation. RNA was extracted from the yeast essentially the same way as with *E. coli* except the RNA was resuspended in 200 microliters of water.

Example 9
2D Northern Blot Analysis of Total *E. coli* and *S. cerevisiae* RNA

Two dimensional Northern blots were produced by the following method.

First, a two dimensional gel was made as described in Example 6, except the gels were not dried. Five micrograms of RNA sample from Example 8 was used making the 2D gels. The gels were preequilibrated with 1×TNAE buffer (10 mM Tris base, 5 mM sodium acetate, 5 mM EDTA, adjusted to pH 7.8 with glacial acetic acid), and electrobloted onto a nylon transfer membrane (Schleicher and Schuell) at 395 mV for 12 hrs. Nylon filters were dried at room temperature and irradiated with short wave ultraviolet light for 20 min to fix RNA. Filters were pre-incubated in 5 ml of 5×SSC, 5×Denhardt's solution (1×Denhardt's solution is 0.02% ficol, 0.02% polyvinyl pyrollidone, 0.02% BSA), 5 mM EDTA, 0.5% SDS, 250 mg/ml sonicated herring sperm DNA, and 50 mM Tris-HCl (pH 8.0) at 45° C. for 30 min. One million counts of $^{32}$p kinased td exon oligonucleotide were added and incubated overnight at 45° C. Filters were then washed three times in 5×SSC and 0.5% SDS, once in 5×SSC, and autoradiographed.

The blots shown in FIGS. 6 and 7 show that the current invention produces the desired exon circles in vivo from the following constructs. FIG. 6 shows that the 71 nt and 100 nt circles from the pEFC-ΔNde construct are produced in *E. coli*. FIG. 7A shows that the same circles as in FIG. 6 are produced from the pΔN-Y(+) construct in yeast. FIG. 7B shows that a circle of 184 nt and 155 nt, from the pΔN-G (+)-A(+), are produced from correct group I splicing and use of the 5' alternative splice site respectively. The two major circular product in FIG. 7B consist of the td exon sequence and the actin exon sequence of pΔN-A(+)-G(+) with their difference being the larger circle is produced from use of the correct 5' splice site and the smaller circle from use of the 5' cryptic splice site.

Example 10
Construction of Plasmid pEFtd

This example illustrates the construction of plasmid pEFtd.

Plasmid pEFtd was created by inserting the 957bp EcoR1-Xba1 fragment of pTZtd18-1 into the pTZtd18-2 that had been cut with EcoR1 and Xba1, as described in *J. Mol. Biol.*, 211:537 (1990) and according to the methods in *Current Protocols in Molecular Biology*, ibid. This plasmid contains the T4 td gene in its natural form, two discontinuous exons divided by a single continuous intron along with the tandem lac and T7 promoters for transcription in vivo in *E. coli* and in vitro, respectively. Upon transcription and group I splicing this construct produces ligated linear exons and excised linear intron which can undergo a circularization reaction, not to be confused with the exon circularization reaction of the current invention.

Example 11
Construction of Plasmid DEFC

This example illustrates preparation of plasmid PEFC.

Plasmid pEFC was created by inserting the 580 bp Sph1-Xba1 fragment of pTZtd18-2 into the unique EcoR1 site of pTZtd18-1 according to the methods in *Current protocols in Molecular Biology*, ibid. This plasmid contains the tandem lac and phage T7 promoters. Downstream of the promoters in the 5' to 3' direction is the 3' half of the intron, the 3' splice site, exon 2, exon 1, the 5' splice site, and the 5' half of the intron. This plasmid, upon transcription and group I splicing, creates intron products and the circularized exon of the current invention.

Example 12
Preparation of Plasmid pEFCΔNde

This example illustrates construction of plasmid pEFCΔNde.

Plasmid pEFCΔNde was created by cutting plasmid pEFC with Nde1 and ligating the large fragment back together according to the methods in *Current protocols in Molecular Biology*, ibid.

This construct is the same as PEFC except that all but 100 nt of the exon sequence are deleted. This construct is a prototype plasmid containing an RNA cyclase ribozyme gene because it contains a small amount of td exon sequence and contains a unique Nde1 site to insert the sequence to be rendered circular. This construct represents the current RNA cyclase invention. It is shown to produce circular exon RNA in vitro as seen in FIG. 4A and in vivo as seen in FIG. 6.

Example 13
Construction of Plasmid pΔNAct(+) This example illustrates construction of plasmid pΔNAct(+). Plasmid pΔNAct(+) was created by inserting the 452 bp Smal-HindIII fragment of pT7Act into the Nde1 site of pEFCΔNde, according to the Methods in *Current protocols in Molecular Biology*, ibid. In this construct, the actin intron with a small amount of actin exon was inserted into the Nde1 site of pEFCΔNde. This construct contains, as the tandem lac and T7 promoters. The primary RNA transcript from these promoters contains, in the 5' to 3' direction, the 3' half of the td intron, td exon sequence, sequence from actin exon 1, the actin intron, sequence from actin exon 2, td exon sequence, and the 5' half of the td intron. Upon group I splicing, this construct creates td intron product and a circular exon product containing the inserted actin sequence joined by ligated 100 nt td exon sequence found in pEFCΔNde. This example shows that a sequence can be inserted into the Nde1 site of pEFCΔNde a be rendered circular. This construct produced large amounts of the circular RNA molecule described above in vitro as seen in FIG. 4B.

Example 14
Construction of Plasmid pΔN-Y(+)

This example illustrates preparation of plasmid pΔN-Y(+).

Plasmid pΔN-Y(+) was created by inserting the 499 bp XbaI fragment of pEFCΔNde into pYES1.2 (Invitrogen, San Diego). This plasmid contains the RNA cyclase ribozyme gene in the context of elements necessary for expression in yeast. This consists of the 3' half of the td intron, 100 nt of td exon sequence, and the 5' half of the intron, inserted into the 2m yeast expression vector pYES1.2 (Invitrogen, San Diego), This construct adds 70 nt of GAL1 5' untranslated (leader) sequence as well as 155 nt of CYC1 3' untranslated sequence. These extra sequences and a poly(A) tail are added to the site of the phosphate backbone discontinuity at P6a and P6a' respectively.

The demonstration of RNA cyclase activity in this example and in Example 15 shows that the RNA cyclase ribozyme can be used as a cassette, and inserted between elements necessary for efficient expression of eukaryotic genes without interfering with either efficient expression or RNA cyclase activity.

In the same manner, the corresponding constructs will function with the necessary elements for expression of mammalian, plant, and other eukaryotic cells.

Example 15
Construction of Plasmid pΔN-A(+)-(G+)

This example illustrates construction of plasmid pΔN-A (+)-(G+).

Plasmid pΔN-A(+)-G(+) was created by inserting the 947 bp Xba fragment of pΔNAct(+) into pYES1.2. This plasmid contains the same RNA cyclase ribozyme gene as plasmid pΔNAct(+), as seen in Example 13, except that the above construct is present in the yeast expression vector pYES1.2 for expression in *S. cerevisiae* as seen in FIG. 2E. The transcripts from this construct produces a similar RNA cyclase ribozyme as from pΔNAct(+) but differ in the addition of the elements necessary for expression in *S. cerevisiae* described above in Example 13.

Transcripts from plasmid pΔN-A(+)-G(+) were shown to undergo group I splicing in *S. cerevisiae* efficiently and produce circular RNA as seen in FIG. 7B.

This example shows that the current invention is capable of functioning in *S. cerevisiae* and most likely other eukaryotes as described in Example 14.

Example 16

Construction of plasmid pRR1

This example illustrates the construction of pRR1.

Plasmid pEFCΔNde was introduced into *E. coli* strain CJ236 by selecting for ampicillin resistance (Example 1). Single stranded DNA of plasmid pEFCΔNde was extracted and used for oligonucleotide directed mutagenesis according to the methods in *Current Methods in Molecular Biology*, ibid., in order to delete and replace the td exon sequences.

The oligonucleotide used to create the mutation was purchased from Genset (La Jolla, Calif.) where it was synthesized chemically using standard techniques. The oligonucleotide is 64 residues long, has the following sequence, which is complementary to the region of the exon and splice sites of pEFCΔNde and changes these sequences to those found in pRR1:

5' CTCAGGCCTCAATTGACCTGAGATC-
TATCGATGGTACCTCGAGCTCCATGGTAGC
ATTATGTTC3'. (SEQ ID NO. 7).

The correct replacement of the sequence in pEFCΔNde with that of the oligo to create pRR1 was confirmed by dideoxy DNA sequencing of the double stranded pRR1 plasmid DNA according to the methods in *Current Methods in Molecular Biology*, ibid.

This example confirms that all intron sequences are deleted from the circularized product and that there are no extra nucleotides present in the circular RNA.

What is claimed is:

1. A method for producing a circular RNA, said method comprising the steps of:
   (a) providing a target nucleic acid sequence to be made circular;
   (b) making a DNA construct encoding an RNA cyclase ribozyme, wherein the arrangement of regions that code for RNA cyclase ribozyme splicing elements is an encoded 3' portion of an intron, an encoded 3' splice site, the target nucleic acid sequence of step (a), an encoded 5' splice site and an encoded 5' portion of the intron;
   (c) expressing the DNA construct as an RNA; and,
   (d) allowing the RNA to self-splice, thereby producing the circular RNA.

2. The method of claim 1, wherein the DNA construct is a plasmid and the target nucleic acid is inserted into an exon of the plasmid in a site of a polylinker in the exon using a procedure selected from the group of procedures consisting of cloning, the polymerase chain reaction, and oligonucleotide directed mutagenesis.

3. The method of claim 2, wherein nucleotides of the polylinker are removed from the plasmid by oligonucleotide directed mutagenesis or by deletion using restriction enzymes.

4. The method of claim 3, wherein the plasmid is expressed in vivo in cells in culture by transcription after introduction of the plasmid into the cells by transformation, viral transduction, microinjection, electroporation or liposome mediated transformation.

5. The method of claim 3, wherein the plasmid is expressed by in vitro transcription.

6. The method of claim 5, wherein the in vitro transcription comprises encoding a transcription termination site at the end of the 5' portion of the intron and by initiating RNA transcripts in the 3' portion of the intron which are transcribed to encode RNA corresponding to the 3' splice site, the target nucleic acid sequence, 5' splice site and the 5' portion of the intron.

7. The method of claim 4, wherein the RNA cyclase ribozyme splicing elements are derived from group I self-splicing introns.

8. The method of claim 7, wherein the group I self-splicing intron is bacteriophage T4 td intron.

9. The method of claim 1, wherein the circular RNA is produced either in vitro, or in vivo in cell in culture.

10. The method of claim 9, wherein the circular RNA is produced in yeast.

11. The method of claim 9, wherein the circular RNA is produced in bacteria.

12. A circular RNA of a nucleic acid sequence produced by a method comprising the steps:
   (a) providing a target nucleic acid sequence to be made circular;
   (b) making a DNA construct encoding an RNA cyclase ribozyme, wherein the arrangement of regions that code for RNA cyclase ribozyme splicing elements is an encoded 3' portion of an intron, an encoded 3' splice site, the target nucleic acid sequence of step (a), an encoded 5' splice site and an encoded 5' portion of the intron;
   (c) expressing the DNA construct as an RNA; and,
   (d) allowing the RNA to self-splice in a circular form to produce said circular RNA.

13. A method of making a repeating protein product from a circular RNA, the method comprising the steps:
   (a) providing a nucleic acid sequence to be made circular;
   (b) making a DNA construct encoding an RNA cyclase ribozyme, wherein the arrangement of regions that code for RNA cyclase ribozyme splicing elements is an encoded 3' portion of an intron, an encoded 3' splice site, the nucleic acid sequence of step (a), an encoded 5' splice site and an encoded 5' portion of the intron;
   (c) expressing the plasmid as RNA; and
   (d) allowing the RNA to selfsplice, thereby producing a circular RNA; and
   (e) translating the circular RNA in an appropriate translation system, thereby producing a repeating protein product from the circular RNA.

14. A plasmid for producing a circular RNA having an arrangement of the regions that code for the splicing elements that constitute an RNA cyclase ribozyme, wherein said arrangement is a 3' portion of an encoded intron, an encoded 3' splice site, a target nucleic acid, an encoded 5' splice site and a 5' portion of the intron.

15. The plasmid of claim 14, wherein the plasmid is pEFC created by inserting the 580 bp Sph1-Xba1 fragment of pTZtd18-2 into the unique EcoR1 site of pTZtd18-1 containing the tandem lac and phage T7 promoters.

16. The plasmid of claim 14, wherein the plasmid is pEFCΔNde created by cutting plasmid pEFC with Nde1 and ligating the large fragment back together, further containing a minimal amount of td exon sequence and a unique Nde1 site.

17. The plasmid of claim 14, wherein the plasmid is pEFC-ΔNAct(+) created by inserting the 452 bp Sma1-HindIII fragment of pT7Act into the Nde1 site of pEFCΔNde, further containing the tandem lac and T7 promoters.

18. The plasmid of claim 14, wherein the plasmid is pΔN-Y(+) created by inserting the 499 bp xbaI fragment of pEFCΔNde into pYES.

19. The plasmid of claim 14, wherein the plasmid is pΔN-A(+)-G(+) created by inserting the 452 bp Sma1-HindIII fragment of pT7Act into pΔN-Y(+).

20. The plasmid of claim 14, wherein the plasmid is pRR1.

21. A nucleic acid encoding an RNA cyclase ribozyme with the following arrangement of elements: a 3' portion of an intron, a 3' splice site, a nucleic acid subsequence which encodes a polypeptide, a 5' splice site and a 5' portion of the intron.

22. An RNA encoded by the nucleic acid of claim 21.

23. A DNA construct encoding the nucleic acid of claim 21.

24. A cell comprising the nucleic acid of claim 21.

25. A method of making a circular RNA comprising expressing an RNA encoded by the nucleic acid of claim 21 in a cell in culture and permitting the RNA encoded by the nucleic acid to self-splice, thereby producing a circular RNA.

26. The nucleic acid of claim 21, wherein the intron is a group I intron.

* * * * *